US012303489B2

(12) United States Patent
Jonassen

(10) Patent No.: US 12,303,489 B2
(45) Date of Patent: May 20, 2025

(54) COMBINATION TREATMENT OF ARTHRITIC DISEASE

(71) Applicant: SYNACT PHARMA APS, Holte (DK)

(72) Inventor: Thomas Engelbrecht Nordkild Jonassen, Holte (DK)

(73) Assignee: Synact Pharma APS, Holte (DK)

( * ) Notice: Subject to any disclaimer, the term of this patent is extended or adjusted under 35 U.S.C. 154(b) by 769 days.

(21) Appl. No.: 17/609,849

(22) PCT Filed: May 7, 2020

(86) PCT No.: PCT/EP2020/062711
§ 371 (c)(1),
(2) Date: Nov. 9, 2021

(87) PCT Pub. No.: WO2020/229097
PCT Pub. Date: Nov. 19, 2020

(65) Prior Publication Data
US 2022/0211666 A1 Jul. 7, 2022

(30) Foreign Application Priority Data
May 10, 2019 (EP) .................................... 19173734

(51) Int. Cl.
A61K 31/402 (2006.01)
A61K 9/00 (2006.01)
A61K 31/519 (2006.01)
A61P 19/02 (2006.01)
A61P 29/00 (2006.01)

(52) U.S. Cl.
CPC .......... A61K 31/402 (2013.01); A61K 31/519 (2013.01); A61P 19/02 (2018.01); A61P 29/00 (2018.01); A61K 9/0053 (2013.01)

(58) Field of Classification Search
CPC ......................... A61K 31/402; C07D 207/335
USPC .................................. 514/427, 249; 548/561
See application file for complete search history.

(56) References Cited

U.S. PATENT DOCUMENTS

| | | | |
|---|---|---|---|
| 6,632,815 B2 | 10/2003 | Zhu et al. | |
| 6,686,368 B1 | 2/2004 | Zhu et al. | |
| 6,720,317 B1 | 4/2004 | Zhu et al. | |
| 6,844,367 B1 | 1/2005 | Zhu et al. | |
| 7,153,881 B2 | 12/2006 | Lundstedt et al. | |
| 7,186,748 B2 * | 3/2007 | Lundstedt | A61P 35/00 514/427 |
| 7,285,565 B2 | 10/2007 | Zhu et al. | |
| 7,442,807 B2 | 10/2008 | Lundstedt et al. | |
| 8,372,878 B2 | 2/2013 | Lundstedt et al. | |
| 9,662,807 B2 | 5/2017 | Feeney et al. | |
| 9,794,214 B2 | 10/2017 | Banatwala et al. | |
| 10,387,927 B2 | 8/2019 | O'Connor et al. | |
| 2003/0211150 A1 | 11/2003 | Al-Ghazawi et al. | |
| 2009/0018183 A1 | 1/2009 | Lundstedt et al. | |
| 2011/0082183 A1 | 4/2011 | Boman et al. | |
| 2021/0121418 A1 | 4/2021 | Jonassen | |
| 2023/0211150 A1 | 7/2023 | He | |

FOREIGN PATENT DOCUMENTS

| | | |
|---|---|---|
| GB | 2398299 A | 8/2004 |
| WO | 98/23267 A1 | 6/1998 |
| WO | 99/21571 A1 | 5/1999 |
| WO | 99/55679 A1 | 11/1999 |
| WO | 99/64002 A1 | 12/1999 |
| WO | 00/58361 A1 | 10/2000 |
| WO | 00/74679 A1 | 12/2000 |
| WO | 01/05401 A1 | 1/2001 |
| WO | 2001/019788 A2 | 3/2001 |
| WO | 2001/019798 A2 | 3/2001 |
| WO | 01/55106 A2 | 8/2001 |
| WO | 01/55107 A2 | 8/2001 |
| WO | 01/55109 A1 | 8/2001 |
| WO | 01/74679 A1 | 10/2001 |
| WO | 02/11715 A2 | 2/2002 |
| WO | 02/12166 A2 | 2/2002 |
| WO | 02/12178 A1 | 2/2002 |
| WO | 02/18327 A2 | 3/2002 |
| WO | 2002/069905 A2 | 9/2002 |
| WO | 03/13509 A1 | 2/2003 |
| WO | 2007/059188 A1 | 5/2007 |
| WO | 2007/141343 A1 | 12/2007 |
| WO | 2008/071980 A1 | 6/2008 |
| WO | 2009/039859 A1 | 4/2009 |
| WO | 2009/071101 A1 | 6/2009 |
| WO | 2009/074157 A1 | 6/2009 |
| WO | 2011/111143 A1 | 9/2011 |
| WO | 2014/060606 A1 | 4/2014 |
| WO | 2015/162483 A1 | 10/2015 |

(Continued)

OTHER PUBLICATIONS

Wolff et al., "Burger's Medicinal Chemistry and Drug Discovery," 5th Ed. Part 1, pp. 975-977 (1995). (Year: 1995).*
Banker, et al., (1996), Modern Pharmaceuticals, p. 596. (Year: 1996).*
Clin Exp Rheumatol. Sep.-Oct. 2010; 28(5 Suppl 61): S52-7. (Year: 2010).*
Rath et al., Clin Exp Rhetamol, Sep.-Oct. 2010, vol. 28(5 Suppl 61), 852-7 (Year: 2010).*
Qiao et al., "MC1R is Dispensable for the Proteinuria Reducing and Glomerular Protective Effect of Melanocortin Therapy", Nature Scientific Reports, 2016, vol. 6, 27589.

(Continued)

Primary Examiner — Jeffrey H Murray
Assistant Examiner — Rilla Marie Samsell
(74) Attorney, Agent, or Firm — BakerHostetler

(57) ABSTRACT

The present invention relates to a composition comprising, separately or together, methotrexate (MTX) and (E)-N-trans-{3-[1-(2-nitrophenyl)-1H-pyrrol-2-yl]-allylidene}-aminoguanidinium acetate (AP1189), or pharmaceutically acceptable derivatives thereof, for use in a method of treating an arthritis disease, such as rheumatoid arthritis.

18 Claims, 2 Drawing Sheets

(56) References Cited

FOREIGN PATENT DOCUMENTS

| WO | 2015/162486 A1 | 10/2015 |
|---|---|---|
| WO | 2019/243625 A1 | 12/2019 |
| WO | 2020/107221 A1 | 6/2020 |
| WO | 2020/229297 A1 | 11/2020 |

OTHER PUBLICATIONS

Rooney et al., "Changes in Synovial in Lymphocyte Infiltration of the Membrane and the Clinical Course of Rheumatoid Arthritis", Arthritis Rheum., 1989, 32, 361-369.
Roselli-Rehfuss et al., "Identification of a receptor for y melanotropin and other proopiomelanocortin peptides in the hypothalamus and limbic system", Proc. Natl. Acad. Sci., USA, Oct. 1993, vol. 90, 8856-8860.
Salaffi et al., Disease Activity assessment of rheumatoid arthritis in daily practice: Validity, Internal Consistency, Reliability and Congruency of the Disease Activity Score Including 28 Joints (DAS28) Compared with the Clinical Disease Activity Index (CDAI), Jul.-Aug. 2009, 27(4), 552-559.
Schioth et al., "Characterization of the binding of MSH.B, HP.228, GHRP.6 and 153N-6 to the human melanocortin receptor subtypes", Neuropeptides, 1997, 31, 565-571.
Schwartz, "Orexins and appetite: The big picture of energy homeostasis gets a little bigger", Nature Medicine, 1998, 4, 385-386.
Sergeant et al., "Prediction of primary non-response to methotrexate therapy using demographic, clinical and psychosocial variables: results from the UK Rheumatoid Arthritis Medication Study (RAMS)", Arthritis Research & Therapy, 2018, 20, 147.
Siegrist et al., "Radioreceptor Assay For a-MSH Using Mouse 816 Melanoma Cells+", J. Recept. Res., 1988, 8(1-4), 323-343.
Silman et al., "Supplement Review: Epidemiology and genetics of rheumatoid arthritis", Arthritis Res., 2002, 3 Supple. 3, S265-272.
Slominski et al., "Corticotropin Releasing Hormone and Proopiomelanocortin Involvement in the Cutaneous Response to Stress Physcol.", Review, Jul. 2000, vol. 80, No. 3, 979-1020.
Tamura et al., "Soluble interleukin-6 receptor triggers osteoclast formation by interleukin 6", Proc. Natl. Acad. Sci. USA, 1993, 90, 11924-11928.
Taub, "Hepatoprotection via the IL-6/Stat3 Pathway", J. Clin. Invest., 2003, 112, 978-980.
Taylor et al., "In vitro induction of CD25+ CD4+ regulatory T cells by the neuropeptide alpha-melanocyte stimulating hormone (a-MSH)", Immunology and Cell Biology, 2001, 79, 358-367.
The Science and Practice of Pharmacy, 19 Edition, Gennaro, Ed., Mack Publishing Co., Easton, PA., 1995.
Thody et al., "Short Communications: The Pituitary and Sebaceous Gland Activity", J. Endocr., 1970, 48, 139-140.
U.S. Appl. No. 60/154,332, entitled Inhibitors of Factor XA, filed on Sep. 17, 1999.
van der Kraan et al., "Expression of Melanocortin-5 Receptor in Secretory Epithelia Supports a Functional Role in Exocrine and Endocrine Glands", Endocrinol., 1998, 139, 2348-2355.
Vand der Ploeg et al., "A role for the melanocortin 4 receptor in sexual function", Proc., Natl., Acad. Sci. USA, Aug. 2002, vol. 99, No. 17, 11381-11386.
Vandenberk et al., "Which QT Correction Formulae to Use for QT Monitoring?", Journal of the American Heart Association, 2016, 5, e003264.
Vergoni et al., "Corticotropin Inhibits Food Intake IN Rats", Neuropeptides, 1986, 7, 153-158.
Vergoni et al., "Differential Influence of a Selective Melanocortin MC Receptor 4 Antagonist (HS014) on Melanocortin-induced Behavioral Effects in Rats", Eur. J. Pharmacol., 1998, 362, 95-101.
Walters et al., "An investigation of the action of disease modifying antirheumatic drugs on the rheumatoid synovial membrane: Reduction in T lymphocyte subpopulations and HLA-DP and DQ antigen expression after gold or penicillamine therapy", Ann Rheum Dis, 1987, 46, 7-16.
Weinblatt, "Methotrexate in Rheumatoid Arthritis: A Quarter Century of Development", Trans. Am. Clin. Climatol. Assoc., 2013, p. 16-25.
Xia et al., "Localization of ACTH receptor mRNA by in situ hybridization in mouse adrenal gland", Cell & Tissue Research, 1996, 286, 63-68.
Yanni et al., "Intramuscular gold decreases cytokine expression and macrophage numbers in the rheumatoid synovial membrane", Ann Rheum Dis, 1994, 53, 315-322.
Youssef et al., "Effects of Pulse Methylprednisolone on Inflammatory Mediators in Peripheral Blood, Synovial Fluid, and Synovial Membrane in Rheumatoid Arthritis", Arthritis Rheum, Aug. 1997, vol. 40, No. 8, 1400-1408.
Youssef et al., "Neutrophil Trafficking into Inflamed Joints in Patients with Rheumatoid Arthritis, and the Effects of Methylprednisolone", Arthritis Rheum, Feb. 1996, vol. 39, No. 2, 216-225.
Vengerovsky, "Pharmacological incompatibility", Bulletin of Siberian Medicine, No. 3, 2003, pp. 49-56.
Tallarida, "Quantitative Methods for Assessing Drug Synergism", Genes & Cancer, 2011, vol. 2, No. 11, pp. 1003-1008.
Abdel-Malek et al., "Mitogenic and Melanogenic Stimulation of Normal Human Melanocytes by Melanotropic Peptides", Proc. Natl. Acad. Sci. USA, Feb. 1995, vol. 92, 1789-1793.
Abdel-Malek, "Melanocortin receptors: their functions and regulation by physiological agonists and antagonists", Cellular and Molecular Life Science, Nov. 2001, 58, 434-441.
Alvaro et al., "Morphine Down-regulates Melanocortin-4 Receptor Expression in Brain Regions that Mediate Opiate Addiction", Molecular Pharmacology, Jan. 1996, 50, 583-591.
Berge et al., "Pharmaceutical Salts", J. Pharm. Sci., Jan. 1977, 66, 1, 1-19.
Blumberg et al., "Rheumatoid Arthritis: Guidelines for Emerging Therapies", Am. J. Manag. Care, Jun. 2001, 7(6), 617-626.
Boston, "The Role of Melanocortins in Adipocyte Function", Annals New York Academy of Sciences, 1999, 75-84.
Bresnihan et al., "Synovial tissue analysis in rheumatoid arthritis", Ballieres Clin. Rheumatol. 1999, 13, 645-659.
Brzoska et al., "a-Melanocyte-Stimulating Hormone and Related Tripeptides: Biochemistry, Anti-inflammatory and Protective Effects in Vitro and in Vivo, and Future Perspectives for the Treatment of Immune-Mediated Inflammatory Diseases", Endocr. Rev., Aug. 2008, 29, 581-602.
Buckley et al., "Isolation of a-Melanotropin and N, 0-Diacetylserine' -a-Melanotropin From Porcine Pituitary Extracts", Int. Journal Peptide Protein Research, 1981, 17, 508-513.
Catania et al., "a-Melanocyte Stimulating Hormone in the Modulation of Host Reactions", Endocr. Rev., Oct. 1993, 14(5), 564-576.
Catania et al., "Targeting Melanocortin Receptors as a Novel Strategy to Control Inflammation", Pharmacological Reviews, 2004, vol. 56, No. 1, 1-29.
Chen et al., "Exocrine Gland Dysfunction in MC5-R-Deficient Mice: Evidence for Coordinated Regulation of Exocrine Gland Function by Melanocortin Peptides", Cell, Dec. 1997, vol. 91, 789-798.
Chen et al., "Inactivation of the mouse melanocortin-3 receptor results in increased fat mass and reduced lean body mass", Nature Genetics, Sep. 2000, vol. 26, 97-102.
Chhajlani et al., "Identification of Ligand Binding Residues in Extracellular Loops of the Melanocortin 1 Receptor", Biochem and Biophysical Research Communications, 1996, 219, 521-525.
De Wildt et al., "Effect of y2-Melanocyte-Stimulating Hormone on Cerebral Blood Flow in Rats", J. Cardiovascular Pharmacology, 1995, 25, 989-905.
Ditzel, "Trends The K/BxN mouse: A model of human inflammatory arthritis", Mol Med, 2004, 10, 40-45.
Dolhain et al., Methotrexate Reduces Inflammatory Cell Number, Expression of Monokines and of Adhesion Molecules in Synovial Tissue of patients with Rheumatoid Arthritis, Br. J. Rheumatol., 1998, 37, 502-508.
Donovan, "The behavioural actions of the hypothalamic peptides: a review", Physchol. Med, 1978, 8, 305-316.

(56) References Cited

OTHER PUBLICATIONS

Elvin et al., "Melanocortin 1 Receptor Agonist Protects Podocytes Through Catalase and RhoA Activation", Am. J. Physiol., 2016, vol. 310, No. 9, p. F848-856.

Firestein et al., "Gene Expression (Collagenase, Tissue Inhibitor of Metalloproteinases, Complement, and HLA-DR) in Rheumatoid Arthritis and Osteoarthritis Synovium", Rheum., 1991, 34, 1094-1105.

Firestein et al., Mechanisms of Methotrexate Action in Rheumatoid Arthritis, Arthritis Rheum., 1994, vol. 37, No. 2, 193-200.

Gantz et al., "Molecular Cloning of a Novel Melanocortin Receptor", J. Biological Chemistry, Apr. 1993, vol. 268, No. 11, 8246-8250.

Garcia-Borron et al., "Melanocortin-1 receptor structure and functional regulation Pigment", Cell Res., 2005, 18, 393-410.

Getting et al., "MC3-R as a Novel Target for Antiinflammatory Therapy", Drug News Perspect, Feb. 2000, 13(1), 19-27.

Getting, "Melanocortin peptides and their receptors: new targets for anti-inflammatory therapy", Trends in Pharmacological Sciences, Oct. 2002, vol. 23, No. 10, 447-449.

Gibofsky, "Overview of Epidemiology, Pathophysiology, and Diagnosis of Rheumatoid Arthritis", Am. J. Manag. Care, 2012, 18, S295-S302.

Gong, "Leveraging Melanocortin Pathway to Treat Glomerular Diseases", Adv. Chronic Kidney Dis., 2014, vol. 21, No. 2, p. 134-151.

Gruber et al., "ACTH-(4-10) through r-MSH: evidence for a new class of central autonomic nervous system-regulating peptides", Am. J. Physiol., 1989, 257, R681-694.

Guarini et al., "MC3 receptors are involved in the protective effect of melanocortins in myocardial ischemia/reperfusion-induced arrhythmias", Naunyn-Schmiedeberg's Arch Pharmacol., May 2002, 366, 177-182.

Hirano et al., "Excessive production of interleukin 6/B cell stimulatory factor-2 in rheumatoid arthritis", Eur. J. Immunol., 1988, 18, 1797-1801.

Hirano, The biology of interleukin-6. Chem immunol. 1992;51:153-180.

Houssiau et al., "INTERLEUKIN-6 in Synovial Fluid and Serum of Patients With Rheumatoid Arthritis and Other Inflammatory Arthritides", Arthritis Rheum., Jun. 1988, 31, 784-788.

Hunt et al., "Cultured Human Melanocytes Respond to MSH Peptides and ACTH", Pigment Cell Research, 1994, 7, 217-221.

International Conference on Harmonisation of Technical Requirements for Registration of Pharmaceuticals for Human Use, ICH Harmonised Tripartite Guideline, Maintenance of the ICH Guideline on Non-clinical Safety Studies for the conduct of human clinical trials for Pharmaceuticals M3(R1), Current Step 4 version, dated Nov. 9, 2000.

Jonsson et al., "Effects of Melanocortin 1 Receptor Agonists in Experimental Nephropathies", PLOS One, 2014, vol. 9, No. 1, p. e87816.

Keller et al., "Molecular and Cellular Biology of Interleukin-6 and its Receptor Frontiers", Biosci., 1996, 1, 340-357.

Li et al., "Melanocortin Antagonists Define Two Distinct Pathways of Cardiovascular Control by a- and g-Melanocyte-Stimulating Hormones", J. Neuroscience, Aug. 1996, 16(6), 5182-5188.

Lin et al., "A y-Melanocyte Stimulating Hormone-like Peptide Causes Reflex Natriuresis After Acute Unilateral Nephrectomy", Hypertension, Dec. 1987, vol. 10, No. 6, 619-627.

Lindskog et al., "Melanocortin 1 Receptor Agonists Reduce Proteinuria", J. Am. Soc., Nephrol., 2010, 21, 1290-1298.

Madhok et al., "Serum interleukin 6 levels in rheumatoid arthritis: correlations with clinical and laboratory indices of disease activity Arthritis", Rheum., 1993, 52, 232-234.

Manna et al., "a-Melanocyte-Stimulating Hormone Inhibits the Nuclear Transcription Factor NF-kB Activation Induced by Various Inflammatory Agents", J. Immunology, 1998, 161, 2873-2880.

Marsh et al., "Response of melanocortin-4 receptor-deficient mice to anorectic and orexigenic peptides", Nature Genetics, Jan. 1999, vol. 21, 119-122.

Metzger et al., "Reduced body fat and increased hepatic lipid synthesis in mice bearing interleukin-6-secreting tumor", Am. J. Physoil. Endocrinol. Metab., Oct. 2001, vol. 281, E597-E965.

Montero-Melendez et al., "Association between Periodontal Disease and Inflammatory Arthritis Reveals Modulatory Functions by Melanocortin Receptor Type 3", Am. J. Pathology, 2014, 184(8), 2333-2341.

Montero-Melendez et al., "Biased Agonism as a Novel Strategy to Harness the Proresolving Properties of Melanocortin Receptors Without Eliciting Melanogenic Effects", J. Immunol., 2015, 194, 3381-3388.

Montero-Melendez et al., "The Melanocortin Agonist AP214 Exerts Anti-Inflammatory and Proresolving Properties", Am. J. Pathol., 2011, 179, 259-269.

Mountjoy et al., "Localization of the Melanocortin-4 Receptor (MC4-R) in Neuroendocrine and Autonomic Control Circuits in the Brain", Mol. Endo., 1994, vol. 8, No. 10, 1298-1308.

Mountjoy et al., "The Cloning of a Family of Genes That Encode the Melanocortin Receptors", Science, Aug. 1992, vol. 257, 1248-1251.

Perretti et al., "Resolution Pharmacology: Opportunities for Therapeutic Innovation in Inflammation", Trends Pharmacol. Sci., 2015, 36, 737-755.

Poggioli et al., "ACTH-(1-24) and c -MSH Antagonize Feeding Behavior Stimulated by Kappa Opiate Agonists", Peptides, 1986, 7, 843-848.

Japan College of Rheumatology MTX, Treatment Guidelines Formulating Committee, Methotrexate (MTX) Treatment Guidelines in Rheumatoid Arthritis Treatment, 2016, revised "Summary Edition", 2016, pp. 1 to 12.

Nair et al., "A simple practice guide for dose conversion between animals and human", J Basic Clin Pharma, March 2016-May 2016, vol. 7, No. 2, pp. 27-31.

Stoycheff et al., Nephrotic Syndrome in Diabetic Kidney Disease: An Evaluation and Update of the Definition, American Journal of Kidney Diseases, vol. 54, No. 5, Jun. 26, 2009.

Waldman et al., Treatment of Idiopathic Membranous Nephropathy, Journal of American Society of Nephrology, No. 23, 1617-1630, 2012.

Bjerke, Synact Pharma, "AP1189—A new medicine to treat inflammatory diseases", 2018, 15 pages.

O'Dell et al., The New England Journal of Medicine, "Treatment of Rheumatoid Arthritis with Methotrexate Alone, Sulfasalazine and Hydroxychloroquine, or 3 Combination of all Three Medications", vol. 334, No. 20, 1996, 1287-1291.

Tugwell et al., The New England Journal of Medicine, "Combination Therapy with Cyclosporine and Melhotrexate in Severe Rheumatoid Arthritis", vol. 333, No. 3, July 20, 1995, 137-141.

Williams et al., A Controlled Clinical Trial, "Comparison of Auranofin, Methotrexate, and the Combination of Both in the Treatment of Rheumatoid Arthritis", 1992, 259-269.

Galvan et al., "Review of Non-bacterial Infections in Respiratory Medicine: Viral Pneumonia," Arch Bronconeumol., 2015, vol. 51, Issue 11, pp. 590-597.

Zaki et al., "Viral Infections of the Lung," Dail and Hammar's Pulmonary Pathology, 2008, pp. 426-475.

Rui et al., "Pathogenesis and clinical research progress of novel coronavirus pneumonia", 2020, vol. 30, No. 8, pp. 1171-1176.

Wang et al., "Melanocortin Regulation of Inflammation", Front Endocrinol (Lausanne), Oct. 9, 2019, vol. 10, Article 683, pp. 1-15.

Howard, "Preventing and Managing Toxicities of High-Dose Methotrexate," The Oncologist 2016;21:1471-1482.

Williams, "Comparison of Auranofin, Methotrexate, and the Combination of Both in the Treatment of Rheumatoid Arthritis," Arthritis and Rheumatism, vol. 35, No. 3, Mar. 1992, pp. 259-269.

Willkens, "Comparison of Azathioprine, Methotrexate, and the Combination of the Two in the Treatment of Rheumatoid Arthritis,"

(56) References Cited

OTHER PUBLICATIONS

Arthritis and Rheumatism, vol. 38, No. 12, Dec. 12, 1995, pp. 1799-1806.

* cited by examiner

COMBINATION TREATMENT OF ARTHRITIC DISEASE

CROSS REFERENCE TO RELATED APPLICATIONS

This application is the National Stage Application of International Patent Application No. PCT/EP2020/062711, filed May 7, 2020 which claims the benefit of European Patent Application No. 19173734.5, filed May 10, 2019, the entireties of which is are incorporated by reference, herein.

CROSS REFERENCE TO RELATED APPLICATIONS

This application claims the benefit of European Patent Application No. 19173734.5, filed May 10, 2019, the entirety of which is incorporated by reference, herein.

TECHNICAL FIELD

The present invention relates to a composition comprising, separately or together, methotrexate (MTX), or a prodrug thereof, and phenyl pyrrole aminoguanidine derivative compounds such as AP1189, or pharmaceutically acceptable derivatives thereof, for use in a method of treating an arthritis disease, including rheumatoid arthritis (RA).

BACKGROUND

An arthritic disease is a condition that implies damage or inflammation in one or more joints. The condition often presents with pain, swelling, heat, redness and limitation of movement. There are many different forms of arthritic disorders, the most common types being osteoarthritis and rheumatoid arthritis. Osteoarthritis is a degenerative join disease and results from the wearing down of cartilage. Since the cartilage cannot be properly replaced by the body, it may make new bone at the edge of the joint to compensate for the loss of cartilage. This in turn produces bony swellings which are painful because the new bone is stretching the sensitive lining of the pre-existing bone. This condition is common in the fingers. Rheumatoid arthritis (RA) is an autoimmune disorder that primarily affects joints and between 0.5-1% of adults in the developed world are affected by RA. While the cause of rheumatoid arthritis is not clear, it is believed to involve a combination of genetic and environmental factors. The goal of current treatments is to reduce pain and inflammation to improve the quality of life of the patients suffering from the condition. Pain medications, steroids, and non-steroidal anti-inflammatory drugs (NSAIDs) are frequently used as treatment to reduce symptoms. Disease-modifying antirheumatic drugs (DMARDs), such as hydroxychloroquine and in particular methotrexate (MTX), may be employed in an attempt to slow down the progression of disease. However, MTX can be a challenge to properly dosage to avoid side effects, and not all patients respond properly to MTX.

The melanocortin system is a set of neuropeptidergic and immunoendocrine signaling pathways that play an integral role in the homeostatic control of a diverse array of physiological functions, including melanogenesis, stress response, inflammation, immunomodulation and adrenocortical steroidogenesis. It consists of multiple components, including the five G protein-coupled melanocortin receptors: melanocortin receptor 1 (MC1R) to MC5R; peptide ligands: α, β, γ-melanocyte stimulating hormone (α, β, γ-MSH), adrenocorticotropic hormone (ACTH) secreted by the anterior pituitary; and endogenous antagonists. The biological functions of melanocortin system are mediated by the five melanocortin receptors (MCRs), which have distinct tissue distribution, convey different signalling and exert varying biological activities in different organ systems. Adrenocorticotropic hormone (ACTH) is an endogenous peptide hormone and agonist for all melanocortin receptors 1 to 5 (MC1-5R), of which MC2R specifically binds ACTH; steroidogenesis is triggered only by ACTH and mediated via MC2R in the adrenal cortex. Alpha-melanocyte stimulating hormone (αMSH) is a small endogenous peptide hormone, structurally related to ACTH, which binds all of the MCRs except MC2R. MC1R, abundantly expressed by melanocytes in the skin, is a key control point in melanogenesis and determines hair colour.

Peripheral MC1 and MC3 can be pharmacologically activated to induce anti-inflammation. The endogenous agonist α-melanocyte-stimulating hormone (αMSH), like other protective mediators, is released by immune cells to counterbalance proinflammatory signals, thus preventing excessive tissue damage. Therapeutics targeting the receptors MC1 and MC3 will then act by mimicking the body's own protective resources and might be characterized by a lighter burden of side effects.

Current treatments of arthritic disorders, such as treatment of rheumatoid arthritis with methotrexate, often involves risk of side effects and also may not be fully effective when administered alone, and subjects suffering from arthritic disorders are in need of new and efficient treatment regimens.

Phenyl pyrrole aminoguanidine derivatives with activity on the melanocortin receptors are disclosed in WO 2007/141343. One example of such compound is the anti-inflammatory compound AP1189 ((E)-N-trans-{3-[1-(2-nitrophenyl)-1H-pyrrol-2-yl]-allylidene}-aminoguanidium acetate) which was first shown to bind the MC1R (WO 2007/141343) and later was identified as a biased dual agonist at receptors MC1R and MC3R that does not provoke canonical cAMP generation (and hence no MC1R-induced melanogenesis) but instead appear to induce alternative pathways including ERK1/2-phosphorylation and $Ca^{2+}$ mobilization (Montero-Melendez et al. 2015).

SUMMARY

The present inventors have found that the phenyl pyrrole aminoguanidine derivative AP1189 ((E)-N-trans-{3-[1-(2-nitrophenyl)-1H-pyrrol-2-yl]-allylidene}-aminoguanidium acetate), when used in combination with the current standard-care methotrexate (MTX), exhibits significantly superior anti-arthritic effects compared to either of the compounds when administered alone. By provision of a new anti-arthritic combination treatment as disclosed herein, the present inventors provide a therapeutically effective alternative to current anti-arthritic treatments, and an attractive means for potentially reducing MTX toxicity and providing a novel therapeutic management of patients with a low response rate to MTX, such as MTX non-responders.

It is an aspect of the present disclosure to provide a composition comprising, separately or together, methotrexate (MTX), or a pro-drug thereof, and a compound of formula (I) or (Ia):

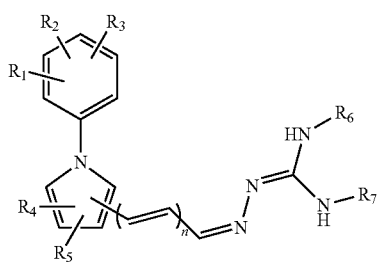

formula (I)

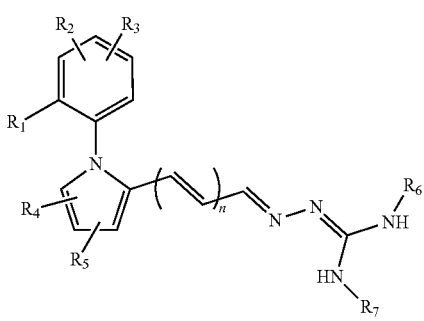

formula (Ia)

including tautomeric and isomeric forms, such as enantiomeric forms, diastereomeric forms and racemic forms, thereof;
wherein
n is 1, 2 or 3;
each $R_1$, $R_2$, $R_3$, $R_4$ and $R_5$ is independently selected from the group consisting of hydrogen, optionally substituted $C_{1-6}$-alkyl, optionally substituted $C_{3-6}$-cycloalkyl, optionally substituted $C_{2-6}$-alkenyl, optionally substituted $C_{4-6}$-alkadienyl, optionally substituted $C_{2-6}$-alkynyl, hydroxy, optionally substituted $C_{1-6}$-alkoxy, optionally substituted $C_{2-6}$-alkenyloxy, carboxy, optionally substituted $C_{1-6}$-alkoxycarbonyl, optionally substituted $C_{1-6}$-alkylcarbonyl, formyl, $C_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroaryloxycarbonyl, optionally substituted heteroaryloxy, optionally substituted heteroarylcarbonyl, optionally substituted heteroarylamino, heteroarylsulphonylamino, optionally substituted heterocyclyl, optionally substituted heterocyclyloxycarbonyl, optionally substituted heterocyclyloxy, optionally substituted heterocyclylcarbonyl, optionally substituted heterocyclylamino, heterocyclylsulphonylamino, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkylamino-$C_{1-6}$-alkyl-aminocarbonyl, $C_{1-6}$-alkylcarbonylamino, amino-$C_{1-6}$-alkyl-carbonylamino, mono- and di($C_{1-6}$-alkyl)amino-$C_{1-6}$-alkyl-carbonylamino, cyano, guanidino, carbamido, $C_{1-6}$-alkanoyloxy, $C_{1-6}$-alkylsulphonyl, $C_{1-6}$-alkylsulphinyl, $C_{1-6}$-alkylsulphonyl-oxy, aminosulfonyl, mono- and di($C_{1-6}$-alkyl)aminosulfonyl, nitro, optionally substituted $C_{1-6}$-alkylthio and halogen, where any nitrogen-bound $C_{1-6}$-alkyl is optionally substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino or guanidine;
each $R_6$ and $R_7$ is independently selected from the group consisting of hydrogen, optionally substituted $C_{1-6}$-alkyl, optionally substituted $C_{2-6}$-alkenyl, optionally substituted $C_{4-6}$-alkadienyl, optionally substituted $C_{2-6}$-alkynyl, optionally substituted $C_{1-6}$-alkoxycarbonyl, optionally substituted $C_{1-6}$-alkylcarbonyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, aminocarbonyl, mono- and di($C_{1-6}$-alkyl)aminocarbonyl, amino-$C_{1-6}$-alkyl-aminocarbonyl and mono- and di($C_{1-6}$-alkyl)amino-$C_{1-6}$-alkyl-aminocarbonyl; or $R_6$ and $R_7$ may together form a five- or six-membered nitrogen-containing ring;
or a pharmaceutically acceptable derivative thereof;
for use in the treatment of an arthritic disease, such as arthritic disease in a subject.

In one embodiment there is provided a composition comprising, separately or together, methotrexate (MTX), or a prodrug thereof, and a compound of formula (II):

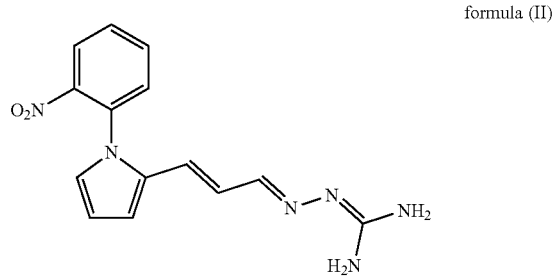 [SMILES: NC(N)=N/N=C/C=C/c1cccn1-c1ccccc1[N+](=O)[O-]]

formula (II)

including tautomeric and isomeric forms, such as enantiomeric forms, diastereomeric
forms and racemic forms, thereof;
or a pharmaceutically acceptable derivative thereof,
for use in the treatment of an arthritic disease.

It is also an aspect of the present disclosure to provide a composition comprising methotrexate (MTX), or a prodrug thereof, and a compound selected from the group consisting of {3-[1-(2-nitrophenyl)-1H-pyrrol-2-yl]-allylidene}-aminoguanidine; {3-[1-(2-nitrophenyl)-1H-pyrrol-2-yl]-allylidene}-aminoguanidinium acetate; (E)-N-trans-{3-[1-(2-nitrophenyl)-1H-pyrrol-2-yl]-allylidene}-aminoguanidine; and (E)-N-trans-{3-[1-(2-nitrophenyl)-1H-pyrrol-2-yl]-allylidene}-aminoguanidinium acetate, or a pharmaceutically acceptable derivative thereof, for use in the treatment of an arthritic disease.

In one embodiment said arthritic disease is rheumatoid arthritis (RA).

Definitions

The term "pharmaceutically acceptable derivative" in the present context includes pharmaceutically acceptable salts, which indicate a salt which is not harmful to the subjects. Such salts include pharmaceutically acceptable basic or acid addition salts as well as pharmaceutically acceptable metal salts, ammonium salts and alkylated ammonium salts. A pharmaceutically acceptable derivative further includes esters and prodrugs, or other precursors of a compound which may be biologically metabolized into the active compound, or crystal forms of a compound.

The term "acid addition salt" is intended to include "pharmaceutically acceptable acid addition salt" which indicates salts which are not harmful to the subject. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 66, 2, (1977) which is incorporated herein by reference.

The term "therapeutically effective amount" of a compound as used herein refers to an amount sufficient to cure, alleviate, prevent, reduce the risk of, or partially arrest the clinical manifestations of a given disease or disorder and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The terms "treatment" and "treating" as used herein refer to the management and care of a subject for the purpose of combating a condition, disease or disorder. The term is intended to include the full spectrum of treatments for a given condition from which the subject is suffering. The subject to be treated is preferably a mammal, in particular a human being. Treatment of animals, such as mice, rats, dogs, cats, horses, cows, sheep and pigs, is, however, also within the scope of the present context. The subjects to be treated can be of various ages.

An "arthritic disease" as referred to herein is an inflammatory disease which presents with joint inflammation. Also known as arthritis.

The term "remission" as used herein refers to reduction or disappearance of the signs and symptoms of the arthritic disease. The remission can be temporary or permanent. Partial remission is a reduction in the signs and symptoms of the arthritic disease, while complete remission is understood herein as a disappearance of the signs and symptoms of the arthritic disease.

DETAILED DESCRIPTION

Figure 1:
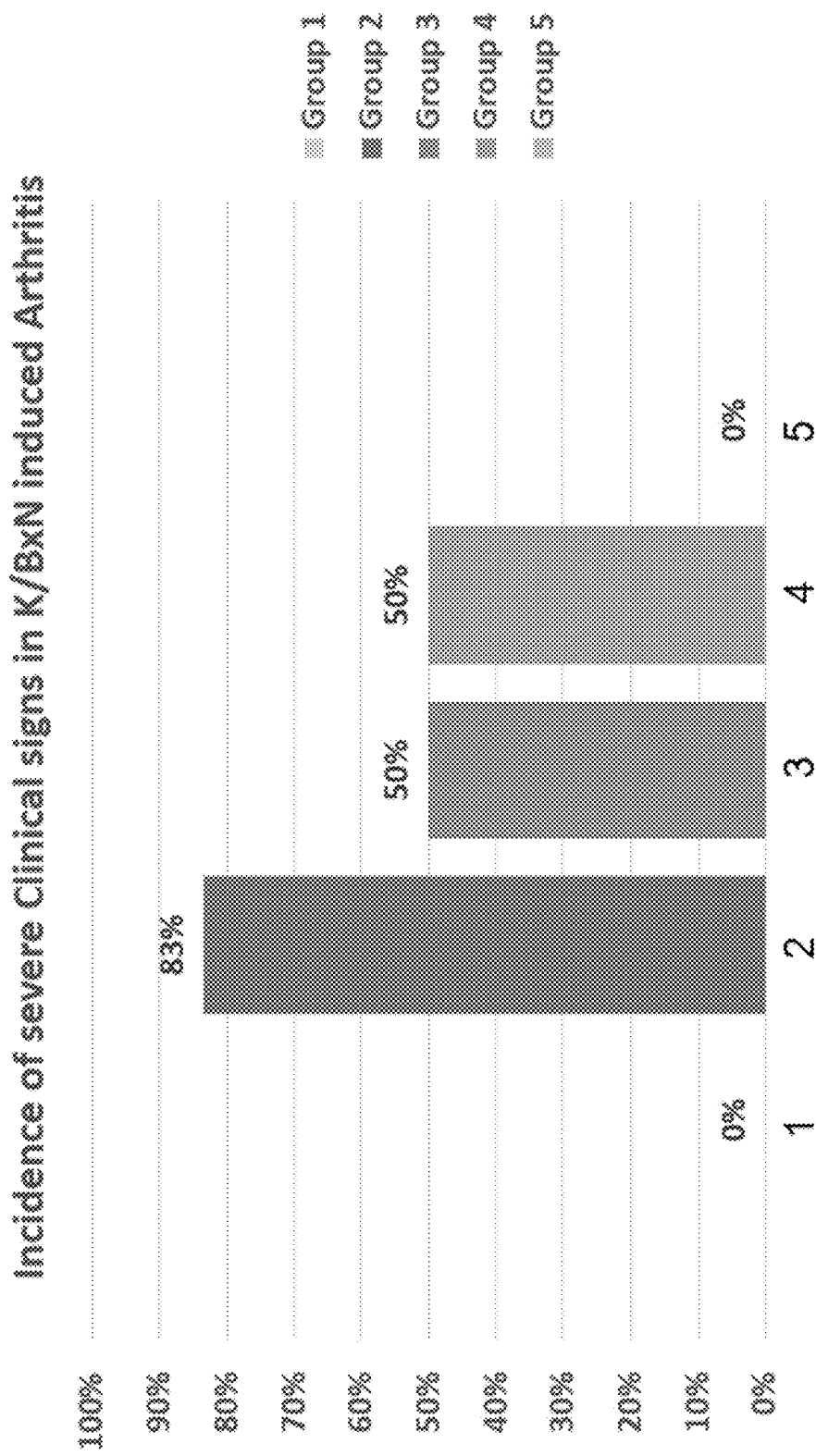
FIG. 1: Percentage of animals who developed severe arthritis defined as clinical score of 10 or higher during the 8 days study period in mice treated with K/BxN serum (for details, see example 1). Group 1: untreated time controls; Group 2: animals treated with vehicle; Group 3: animals treated with Methotrexate; Group 4: animals treated with AP1189; and Group 5: animals treated with a combination of methotrexate and AP1189. Group 3 and Group 5 were treated with identical doses of methotrexate. Group 4 and Group 5 were treated with identical doses of AP1189.

The present disclosure provides a composition comprising, separately or together, methotrexate (MTX) and a compound of formula (I), (Ia) or (II) as defined herein, for treatment of an arthritic disease (or arthritis).

In an aspect of the present disclosure, a composition is provided comprising, separately or together, methotrexate (MTX), or a pro-drug thereof, and
a compound of formula (I) or (Ia):

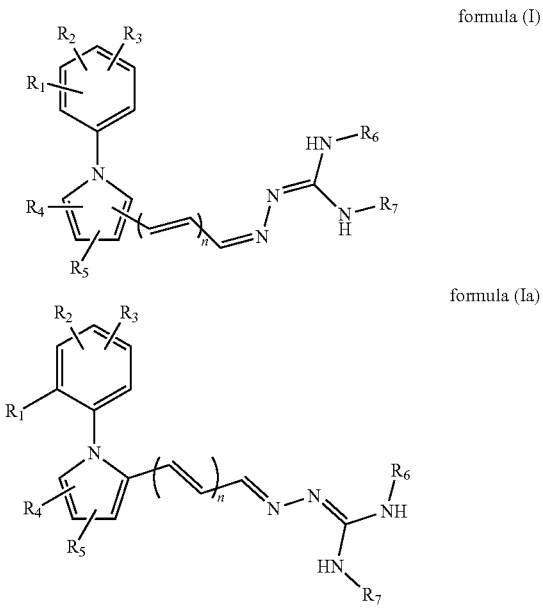

including tautomeric and isomeric forms, such as enantiomeric forms, diastereomeric forms and racemic forms, thereof;

wherein n is 1, 2 or 3;

each $R_1$, $R_2$, $R_3$, $R_4$ and $R_5$ is independently selected from the group consisting of hydrogen, optionally substituted $C_{1-6}$-alkyl, optionally substituted $C_{3-6}$-cycloalkyl, optionally substituted $C_{2-6}$-alkenyl, optionally substituted $C_{4-6}$-alkadienyl, optionally substituted $C_{2-6}$-alkynyl, hydroxy, optionally substituted $C_{1-6}$-alkoxy, optionally substituted C$_{2-6}$-alkenyloxy, carboxy, optionally substituted C$_{1-6}$-alkoxycarbonyl, optionally substituted C$_{1-6}$-alkylcarbonyl, formyl, C$_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroaryloxycarbonyl, optionally substituted heteroaryloxy, optionally substituted heteroarylcarbonyl, optionally substituted heteroarylamino, heteroarylsulphonylamino, optionally substituted heterocyclyl, optionally substituted heterocyclyloxycarbonyl, optionally substituted heterocyclyloxy, optionally substituted heterocyclylcarbonyl, optionally substituted heterocyclylamino, heterocyclylsulphonylamino, amino, mono- and di(C$_{1-6}$-alkyl)amino, carbamoyl, mono- and di(C$_{1-6}$-alkyl)aminocarbonyl, amino-C$_{1-6}$-alkyl-aminocarbonyl, mono- and di(C$_{1-6}$-alkylamino-C$_{1-6}$-alkyl-aminocarbonyl, C$_{1-6}$-alkylcarbonylamino, amino-C$_{1-6}$-alkyl-carbonylamino, mono- and di(C$_{1-6}$-alkyl)amino-C$_{1-6}$-alkyl-carbonylamino, cyano, guanidino, carbamido, C$_{1-6}$-alkanoyloxy, C$_{1-6}$-alkylsulphonyl, C$_{1-6}$-alkylsulphinyl, C$_{1-6}$-alkylsulphonyl-oxy, aminosulfonyl, mono- and di(C$_{1-6}$-alkyl)aminosulfonyl, nitro, optionally substituted C$_{1-6}$-alkylthio and halogen, where any nitrogen-bound C$_{1-6}$-alkyl is optionally substituted with hydroxy, C$_{1-6}$-alkoxy, C$_{2-6}$-alkenyloxy, amino, mono- and di(C$_{1-6}$-alkyl)amino, carboxy, C$_{1-6}$-alkylcarbonylamino, halogen, C$_{1-6}$-alkylthio, C$_{1-6}$-alkyl-sulphonyl-amino or guanidine;

each R$_6$ and R$_7$ is independently selected from the group consisting of hydrogen, optionally substituted C$_{1-6}$-alkyl, optionally substituted C$_{2-6}$-alkenyl, optionally substituted C$_{4-6}$-alkadienyl, optionally substituted C$_{2-6}$-alkynyl, optionally substituted C$_{1-6}$-alkoxycarbonyl, optionally substituted C$_{1-6}$-alkylcarbonyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, aminocarbonyl, mono- and di(C$_{1-6}$-alkyl)aminocarbonyl, amino-C$_{1-6}$-alkyl-aminocarbonyl and mono- and di(C$_{1-6}$-alkyl)amino-C$_{1-6}$-alkyl-aminocarbonyl; or R$_6$ and R$_7$ may together form a five- or six-membered nitrogen-containing ring;

or a pharmaceutically acceptable derivative thereof;

for use in the treatment of an arthritic disease, such as arthritic disease in a subject.

In one embodiment the present disclosure provides methotrexate (MTX), or a pro-drug thereof, and a compound of formula (I) or (Ia), wherein each of n, R$_1$, R$_2$, R$_3$, R$_4$, R$_5$, R$_6$ and R$_7$ are as defined herein, for use in the treatment of an arthritic disease, such as arthritic disease in a subject.

In one embodiment, there is provided a method of treating an arthritic disease comprising one or more steps of administering to a subject, such as a subject in need thereof, a composition comprising, separately or together, methotrexate (MTX), or a pro-drug thereof, and a compound of formula (I) or (Ia):

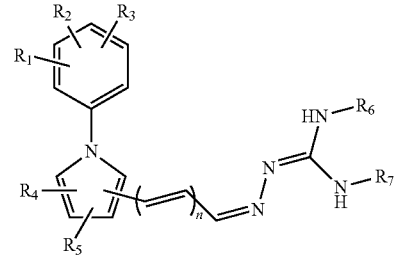

formula (I)

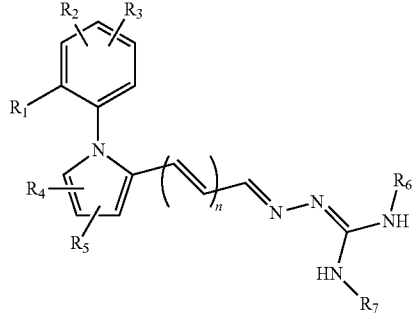

formula (Ia)

including tautomeric and isomeric forms, such as enantiomeric forms, diastereomeric forms and racemic forms, thereof;

wherein n is 1, 2 or 3;

each R$_1$, R$_2$, R$_3$, R$_4$ and R$_5$ is independently selected from the group consisting of hydrogen, optionally substituted C$_{1-6}$-alkyl, optionally substituted C$_{3-6}$-cycloalkyl, optionally substituted C$_{2-6}$-alkenyl, optionally substituted C$_{4-6}$-alkadienyl, optionally substituted C$_{2-6}$-alkynyl, hydroxy, optionally substituted C$_{1-6}$-alkoxy, optionally substituted C$_{2-6}$-alkenyloxy, carboxy, optionally substituted C$_{1-6}$-alkoxycarbonyl, optionally substituted C$_{1-6}$-alkylcarbonyl, formyl, C$_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroaryloxycarbonyl, optionally substituted heteroaryloxy, optionally substituted heteroarylcarbonyl, optionally substituted heteroarylamino, heteroarylsulphonylamino, optionally substituted heterocyclyl, optionally substituted heterocyclyloxycarbonyl, optionally substituted heterocyclyloxy, optionally substituted heterocyclylcarbonyl, optionally substituted heterocyclylamino, heterocyclylsulphonylamino, amino, mono- and di(C$_{1-6}$-alkyl)amino, carbamoyl, mono- and di(C$_{1-6}$-alkyl)aminocarbonyl, amino-C$_{1-6}$-alkyl-aminocarbonyl, mono- and di(C$_{1-6}$-alkylamino-C$_{1-6}$-alkyl-aminocarbonyl, C$_{1-6}$-alkylcarbonylamino, amino-C$_{1-6}$-alkyl-carbonylamino, mono- and di(C$_{1-6}$-alkyl)amino-C$_{1-6}$-alkyl-carbonylamino, cyano, guanidino, carbamido, C$_{1-6}$-alkanoyloxy, C$_{1-6}$-alkylsulphonyl, C$_{1-6}$-alkylsulphinyl, C$_{1-6}$-alkylsulphonyl-oxy, aminosulfonyl, mono- and di(C$_{1-6}$-alkyl)aminosulfonyl, nitro, optionally substituted C$_{1-6}$-alkylthio and halogen, where any nitrogen-bound C$_{1-6}$-alkyl is optionally substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino or guanidine;

each $R_6$ and $R_7$ is independently selected from the group consisting of hydrogen, optionally substituted $C_{1-6}$-alkyl, optionally substituted $C_{2-6}$-alkenyl, optionally substituted $C_{4-6}$-alkadienyl, optionally substituted $C_{2-6}$-alkynyl, optionally substituted $C_{1-6}$-alkoxycarbonyl, optionally substituted $C_{1-6}$-alkylcarbonyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, aminocarbonyl, mono- and di($C_{1-6}$-alkyl)aminocarbonyl, amino-$C_{1-6}$-alkyl-aminocarbonyl and mono- and di($C_{1-6}$-alkyl)amino-$C_{1-6}$-alkyl-aminocarbonyl; or $R_6$ and $R_7$ may together form a five- or six-membered nitrogen-containing ring;

or a pharmaceutically acceptable derivative thereof.

In one embodiment the present disclosure provides a method of treating an arthritic disease comprising one or more steps of administering methotrexate (MTX), or a pro-drug thereof, and one or more steps of administering a compound of formula (I) or (Ia), wherein each of n, $R_1$, $R_2$, $R_3$, $R_4$, $R_5$, $R_6$ and $R_7$ are as defined herein, to a subject, such as a subject in need thereof, In one embodiment of the present disclosure, there is provided the use of a composition comprising, separately or together, methotrexate (MTX), and a compound of formula (I) or (Ia):

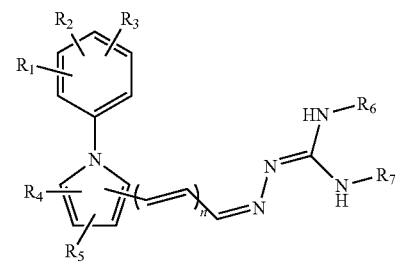

formula (I)

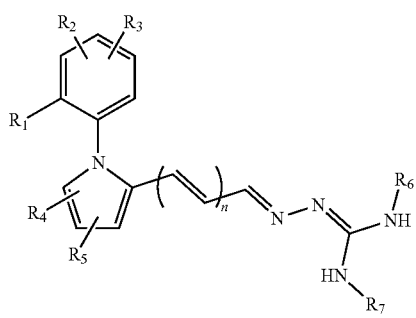

formula (Ia)

including tautomeric and isomeric forms, such as enantiomeric forms, diastereomeric forms and racemic forms, thereof;
wherein
n is 1, 2 or 3;
each $R_1$, $R_2$, $R_3$, $R_4$ and $R_5$ is independently selected from the group consisting of hydrogen, optionally substituted $C_{1-6}$-alkyl, optionally substituted $C_{3-6}$-cycloalkyl, optionally substituted $C_{2-6}$-alkenyl, optionally substituted $C_{4-6}$-alkadienyl, optionally substituted $C_{2-6}$-alkynyl, hydroxy, optionally substituted $C_{1-6}$-alkoxy, optionally substituted $C_{2-6}$-alkenyloxy, carboxy, optionally substituted $C_{1-6}$-alkoxycarbonyl, optionally substituted $C_{1-6}$-alkylcarbonyl, formyl, $C_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroaryloxycarbonyl, optionally substituted heteroaryloxy, optionally substituted heteroarylcarbonyl, optionally substituted heteroarylamino, heteroarylsulphonylamino, optionally substituted heterocyclyl, optionally substituted heterocyclyloxycarbonyl, optionally substituted heterocyclyloxy, optionally substituted heterocyclylcarbonyl, optionally substituted heterocyclylamino, heterocyclylsulphonylamino, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkylamino-$C_{1-6}$-alkyl-aminocarbonyl, $C_{1-6}$-alkylcarbonylamino, amino-$C_{1-6}$-alkyl-carbonylamino, mono- and di($C_{1-6}$-alkyl)amino-$C_{1-6}$-alkyl-carbonylamino, cyano, guanidino, carbamido, $C_{1-6}$-alkanoyloxy, $C_{1-6}$-alkylsulphonyl, $C_{1-6}$-alkylsulphinyl, $C_{1-6}$-alkylsulphonyl-oxy, aminosulfonyl, mono- and di($C_{1-6}$-alkyl)aminosulfonyl, nitro, optionally substituted $C_{1-6}$-alkylthio and halogen, where any nitrogen-bound $C_{1-6}$-alkyl is optionally substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino or guanidine;

each $R_6$ and $R_7$ is independently selected from the group consisting of hydrogen, optionally substituted $C_{1-6}$-alkyl, optionally substituted $C_{2-6}$-alkenyl, optionally substituted $C_{4-6}$-alkadienyl, optionally substituted $C_{2-6}$-alkynyl, optionally substituted $C_{1-6}$-alkoxycarbonyl, optionally substituted $C_{1-6}$-alkylcarbonyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, aminocarbonyl, mono- and di($C_{1-6}$-alkyl)aminocarbonyl, amino-$C_{1-6}$-alkyl-aminocarbonyl and mono- and di($C_{1-6}$-alkyl)amino-$C_{1-6}$-alkyl-aminocarbonyl; or $R_6$ and $R_7$ may together form a five- or six-membered nitrogen-containing ring;

or a pharmaceutically acceptable derivative thereof;

for the manufacture of a medicament for the treatment of an arthritic disease, such as an arthritic disease in a subject.

In one embodiment the present disclosure provides the use of methotrexate (MTX) and a compound of formula (I) or (Ia), wherein each of n, $R_1$, $R_2$, $R_3$, $R_4$, $R_5$, $R_6$ and $R_7$ are as defined herein, for the manufacture of a medicament for the treatment of an arthritic disease.

Compound

The present disclosure provides a combination of methotrexate (MTX), or a pro-drug thereof, and a compound of formula (I) or (Ia), wherein each of n, $R_1$, $R_2$, $R_3$, $R_4$, $R_5$, $R_6$ and $R_7$ are as defined herein above, for use in the treatment of an arthritic disease. In particular embodiment, each of n, $R_1$, $R_2$, $R_3$, $R_4$, $R_5$, $R_6$ and $R_7$ are specified according to the below disclosure.

In one embodiment, n=1. In one embodiment the present disclosure provides a composition comprising, separately or together, methotrexate (MTX), or a pro-drug thereof, and a compound of formula (I) or (Ia), wherein each of $R_1$, $R_2$, $R_3$, $R_4$, $R_5$, $R_6$ and $R_7$ are as defined herein, and n=1, for use in the treatment of an arthritic disease.

In one embodiment each $R_1$, $R_2$ and $R_3$ is independently selected from the group consisting of —H, —CH$_3$, —CF$_3$, —CCl$_3$, —O—C$_{1-6}$ alkyl, —OH, —OCH$_3$, —NH—C$_{1-6}$ alkyl, —N(C$_{1-6}$alkyl)$_2$, —S—C$_{1-6}$ alkyl, —$^t$Bu, —CN, —SO$_3$—C$_{1-6}$ alkyl, —NH$_2$, —NO$_2$, —CO$_2$H, —CO$_2$—C$_{1-6}$ alkyl, —C(═O)—C$_{1-6}$ alkyl, —CHO, morpholine, pyrrolidine, pyrrole, or halogen.

In one embodiment the present disclosure provides a composition comprising, separately or together, methotrexate (MTX), or a pro-drug thereof, and a compound of formula (I) or (Ia), wherein each of n, $R_4$, $R_5$, $R_6$ and $R_7$ are as defined herein, and each $R_1$, $R_2$ and $R_3$ is independently selected from the group consisting of —H, —CH$_3$, —CF$_3$, —CCl$_3$, —O—C$_{1-6}$ alkyl, —OH, —OCH$_3$, —NH—C$_{1-6}$ alkyl, —N(C$_{1-6}$ alkyl)$_2$, —S—C$_{1-6}$ alkyl, —$^t$Bu, —CN, —SO$_3$—C$_{1-6}$ alkyl, —NH$_2$, —NO$_2$, —CO$_2$H, —CO$_2$—C$_{1-6}$alkyl, —C(═O)—C$_{1-6}$ alkyl, —CHO, morpholine, pyrrolidine, pyrrole, or halogen, for use in the treatment of an arthritic disease, such as arthritic disease in a subject.

In one embodiment $R_1$ and/or $R_2$ each is an electron-withdrawing group. In one embodiment the present disclosure provides a composition comprising, separately or together, methotrexate (MTX), or a pro-drug thereof, and a compound of formula (I) or (Ia), wherein each of n, $R_3$, $R_4$, $R_5$, $R_6$ and $R_7$ are as defined herein, and $R_1$ and/or $R_2$ each is an electron-withdrawing group, for use in the treatment of an arthritic disease, such as arthritic disease in a subject.

An electron-withdrawing group is understood as an electron-withdrawing element or functional group that draws electron density from neighbouring atoms towards itself, usually by resonance or inductive effects. Whether a functional group is electron-withdrawing or electron-donating can be determined using the Hammett equation, an equation known to the person skilled in the art. Hammett substituent constants, also known as substituent constants σ can be used as a measure of a functional group's ability to draw electron density from neighboring atoms towards itself. An electron-withdrawing group is an electron-withdrawing element or functional group with a substituent constant σ>0, such as between 0.01 and 0.9 for example 0.78. These values are known in the art and can be found in tables in the scientific literature such as J. Org. Chem., 23, 420 (1958). CF$_3$, CCl$_3$, F, Cl, CN and NO$_2$ are examples of electron-withdrawing groups.

In one embodiment said $R_1$ is selected from the group consisting of CF$_3$, CCl$_3$, F, Cl, CN and NO$_2$. In one embodiment the present disclosure provides methotrexate (MTX), or a pro-drug thereof, and a compound of formula (I) or (Ia), wherein each of n, $R_2$, $R_3$, $R_4$, $R_5$, $R_6$ and $R_7$ are as defined herein, and said $R_1$ is selected from the group consisting of CF$_3$, CCl$_3$, F, Cl, CN and NO$_2$, for use in the treatment of an arthritic disease, such as arthritic disease in a subject.

In one embodiment said $R_2$ and/or $R_3$ each is hydrogen. In one embodiment the present disclosure provides methotrexate (MTX), or a pro-drug thereof, and a compound of formula (I) or (Ia), wherein each of n, $R_1$, $R_4$, $R_5$, $R_6$ and $R_7$ are as defined herein, and $R_2$ and/or $R_3$ each is hydrogen, for use in the treatment of an arthritic disease, such as arthritic disease in a subject.

In one embodiment each $R_4$ and $R_5$ is independently selected from the group consisting of —H, C$_{1-6}$alkyl, halogen, —O(C$_{1-6}$ alkyl), —NH(C$_{1-6}$ alkyl) and —C(═O)C$_{1-6}$ alkyl.

In one embodiment the present disclosure provides methotrexate (MTX), or a pro-drug thereof, and a compound of formula (I) or (Ia), wherein each of n, $R_1$, $R_2$, $R_3$, $R_6$ and $R_7$ are as defined herein, and each $R_4$ and $R_5$ is independently selected from the group consisting of —H, C$_{1-6}$ alkyl, halogen, —O(C$_{1-6}$ alkyl), —NH(C$_{1-6}$ alkyl) and —C(═O) C$_{1-6}$ alkyl, for use in the treatment of an arthritic disease, such as arthritic disease in a subject.

In one embodiment each $R_6$ and $R_7$ is independently selected from the group consisting of hydrogen, methyl, ethyl and propyl.

In one embodiment said $R_6$ and $R_7$ are each hydrogen.

In one embodiment said $R_6$ is hydrogen and $R_7$ is methyl or ethyl. In one embodiment said $R_6$ is hydrogen and $R_7$ is methyl. In one embodiment said $R_6$ is hydrogen and $R_7$ is ethyl. In one embodiment said $R_6$ and $R_7$ are both methyl. In one embodiment said $R_6$ and $R_7$ are both ethyl.

In one embodiment the present disclosure provides methotrexate (MTX), or a pro-drug thereof, and a compound of formula (I) or (Ia), wherein each of n, $R_1$, $R_2$, $R_3$, $R_4$, $R_5$ are as defined herein, and each $R_6$ and $R_7$ is independently selected from the group consisting of hydrogen, methyl, ethyl and propyl, such as wherein
said $R_6$ and $R_7$ are each hydrogen, or
said $R_6$ is hydrogen and $R_7$ is methyl or ethyl, or
said $R_6$ is hydrogen and $R_7$ is methyl, or
said $R_6$ is hydrogen and $R_7$ is ethyl, or
said $R_6$ and $R_7$ are both methyl, or
said $R_6$ and $R_7$ are both ethyl,
for use in the treatment of an arthritic disease, such as arthritic disease in a subject.

In one embodiment said $R_2$, $R_3$, $R_4$, $R_5$, $R_6$ and $R_7$ are each hydrogen, and said $R_1$ is selected from the group consisting of CF$_3$, CCl$_3$, F, Cl, NO$_2$ and CN.

In one embodiment the present disclosure provides methotrexate (MTX), or a pro-drug thereof, and a compound of formula (I) or (Ia), wherein n is 1, 2 or 3, said $R_2$, $R_3$, $R_4$, $R_5$, $R_6$ and $R_7$ are each hydrogen, and said $R_1$ is selected from the group consisting of CF$_3$, CCl$_3$, F, Cl, NO$_2$ and CN, for use in the treatment of an arthritic disease, such as arthritic disease in a subject.

In one embodiment said $R_2$, $R_3$, $R_4$, $R_5$, $R_6$ and $R_7$ are each hydrogen, said $R_1$ is selected from the group consisting of CF$_3$, CCl$_3$, F, Cl, NO$_2$ or CN, and n=1.

In one embodiment the present disclosure provides methotrexate (MTX), or a pro-drug thereof, and a compound of formula (I) or (Ia), wherein n=1, said $R_2$, $R_3$, $R_4$, $R_5$, $R_6$ and $R_7$ are each hydrogen, and said $R_1$ is selected from the group consisting of CF$_3$, CCl$_3$, F, Cl, NO$_2$ and CN, for use in the treatment of an arthritic disease, such as arthritic disease in a subject.

In one embodiment said $R_3$ is located on the 4-position.

In one embodiment said $R_3$ is selected from the group consisting of F, C and Br.

In one embodiment the present disclosure provides methotrexate (MTX), or a pro-drug thereof, and a compound of formula (I) or (Ia), wherein each of n, $R_1$, $R_2$, $R_4$, $R_5$, $R_6$ and $R_7$ are as defined herein, and said $R_3$ is located on the 4-position and/or said $R_3$ is selected from the group consisting of F, C and Br, for use in the treatment of an arthritic disease, such as arthritic disease in a subject.

In one embodiment the present disclosure provides a composition comprising, separately or together, methotrexate (MTX), or a pro-drug thereof, and a compound of formula (II):

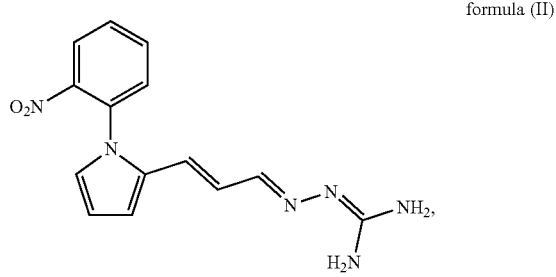 [SMILES: NC(N)=N/N=C/C=C/c1cccn1-c1ccccc1[N+](=O)[O-]]

formula (II)

including tautomeric and isomeric forms, such as enantiomeric forms, diastereomeric forms and racemic forms, thereof; or a pharmaceutically acceptable derivative thereof; for treatment of an arthritic disease, such as arthritic disease in a subject.

In one embodiment said compound is {3-[1-(2-nitrophenyl)-1H-pyrrol-2-yl]-allylidene}-aminoguanidine, preferably (E)-N-trans-{3-[1-(2-nitrophenyl)-1H-pyrrol-2-yl]-allylidene}-aminoguanidine, or a pharmaceutically acceptable derivative thereof, such as a pharmaceutically acceptable salt thereof.

In one embodiment there is provided a composition comprising methotrexate, or a prodrug thereof, and a compound of formula (I), (Ia) or (II) as defined herein including pharmaceutically acceptable derivatives thereof, for use in the treatment of an arthritic disease, wherein the pharmaceutically acceptable derivative thereof is a pharmaceutically acceptable salt of an inorganic acid or a pharmaceutically acceptable salt of an organic acid.

In one embodiment the organic acid is selected from the group consisting of: formic acid, acetic acid, trichloroacetic acid, trifluoroacetic acid, propionic acid, benzoic acid, cinnamic acid, citric acid, fumaric acid, glycolic acid, lactic acid, maleic acid, malic acid, malonic acid, mandelic acid, oxalic acid, picric acid, pyruvic acid, salicylic acid, succinic acid, methanesulfonic acid, ethanesulfonic acid, tartaric acid, ascorbic acid, pamoic acid, bismethylene salicylic acid, ethanedisulfonic acid, gluconic acid, citraconic acid, aspartic acid, stearic acid, palmitic acid, EDTA, glycolic acid, p-aminobenzoic acid, glutamic acid, benzenesulfonic acid and p-toluenesulfonic acid.

In one embodiment said organic acid is acetic acid, succinic acid, tartaric acid or propionic acid.

In one embodiment said inorganic acid is selected from the group consisting of: hydrochloric acid, hydrobromic acid, hydroiodic acid, phosphoric acid, sulphuric acid and nitric acid.

In one embodiment said pharmaceutically acceptable acid is acetic acid.

In one embodiment said compound is {3-[1-(2-nitrophenyl)-1H-pyrrol-2-yl]-allylidene}-aminoguanidinium acetate, preferably (E)-N-trans-{3-[1-(2-nitrophenyl)-1H-pyrrol-2-yl]-allylidene}-aminoguanidinium acetate (AP1189).

In a specific embodiment there is provided a composition comprising, separately or together, methotrexate (MTX) and (E)-N-trans-{3-[1-(2-nitrophenyl)-1H-pyrrol-2-yl]-allylidene}-aminoguanidinium acetate (AP1189) for use in the treatment of an arthritic disease.

In a particular embodiment there is provided a composition comprising, separately or together, methotrexate (MTX) and (E)-N-trans-{3-[1-(2-nitrophenyl)-1H-pyrrol-2-yl]-allylidene}-aminoguanidinium acetate (AP1189), for use in the treatment of rheumatoid arthritis (RA).

In an embodiment there is provided methotrexate (MTX) and (E)-N-trans-{3-[1-(2-nitrophenyl)-1H-pyrrol-2-yl]-allylidene}-aminoguanidinium acetate (AP1189) for use in the treatment of an arthritic disease, such as rheumatoid arthritis.

"(E)-N-trans-{3-[1-(2-nitrophenyl)-1H-pyrrol-2-yl]-allylidene}-aminoguanidinium acetate" and "E-N-[trans-3-{1-(2-nitrophenyl)-1H-pyrrole-2-yl}-allylideneamino] guanidinium acetate" (IUPAC) are used interchangeably herein.

In one embodiment there is provided a composition comprising methotrexate, or a prodrug thereof, and a compound of formula (Ia), wherein said $R_2$, $R_3$, $R_4$ and $R_5$ are each hydrogen, $R_6$ and $R_7$ are each independently selected from the group consisting of hydrogen, methyl, ethyl and propyl, said $R_1$ is selected from the group consisting of $CF_3$, $CCl_3$, F, Cl, $NO_2$ or CN, and n=1 for use in the treatment of an arthritic disease.

In one embodiment there is provided a composition comprising methotrexate, or a prodrug thereof, and a compound of formula (Ia), wherein said $R_2$, $R_3$, $R_4$, $R_5$, $R_6$ and $R_7$ are each hydrogen, said $R_1$ is selected from the group consisting of $CF_3$, $CCl_3$, F, Cl, $NO_2$ or CN, and n=1 for use in the treatment of arthritis.

In one embodiment, the composition for use according to the present disclosure is provided, wherein the composition further comprises one or more pharmaceutically acceptable carriers and/or excipients.

In one embodiment, a composition for use according to the present disclosure is provided, wherein the composition further comprises—separately or together—folic acid, such as folic acid at a dose of at least 5 mg/week. Folic acid can be provided to further minimize MTX toxicity.

In one embodiment the present disclosure provides a composition comprising, separately or together, methotrexate (MTX), or a pro-drug thereof, and a compound of formula (I), (Ia) or (II) as defined herein, for use in the treatment of an arthritic disease, wherein said methotrexate, or a prodrug thereof, is selected from the group consisting of methotrexate (systemic), methotrexate (oral), methotrexate tablet, methotrexate oral solution, methotrexate (injection), methotrexate sodium, Methotrexate LPF Sodium, Trexall (Xatmep), Rheumatrex, Rasuvo, Otrexup, Alltrex, Beltrax, Biotrexate, Caditrex, Carditrex, Cytotrex, Dermotrex, Folitrax, HI-Trex, Imutrex, Merex, Methocip, Methorex, Methotrexate, Metorex, Metrex, Mexate, MTX-Korea, Neotrexate, Nidtrex, Oncotrex, Onotrex, Plastomet, Remtrex, Rextop, Roxate, Tevatrex, Throtex, Trex, Thixilem and Vibzi and Zexate.

Arthritic Disease

The present disclosure provides methotrexate (MTX), or a pro-drug thereof, and a compound of formula (I) or (Ia), wherein each of n, $R_1$, $R_2$, $R_3$, $R_4$, $R_5$, $R_6$ and $R_7$ are as defined herein, for use in the treatment of an arthritic disease, such as arthritic disease in a subject, wherein the arthritic disease is specified herein below.

'Arthritic disease' and 'arthritis' may be used interchangeably herein.

The term arthritis is often used to refer to any disorder that affects the joints. These disorders fall within the broader category of rheumatic diseases. "Arthritis" literally means joint inflammation, which is a symptom of the disease.

In one embodiment the arthritic disease is an autoimmune disease and/or an inflammatory disease that presents with joint inflammation.

In one embodiment, the arthritic disease is selected from the group consisting of inflammatory arthritis, degenerative arthritis, metabolic arthritis, reactive arthritis and infectious arthritis.

In one embodiment, the arthritic disease is inflammatory arthritis. In one embodiment, the inflammatory arthritis is selected from the group consisting of Rheumatoid Arthritis (RA), Psoriatic Arthritis, and Ankylosing Spondylitis.

In one embodiment, the degenerative arthritis is osteoarthritis.

In one embodiment, the metabolic arthritis is gouty arthritis.

In one embodiment, the reactive and/or infectious arthritis is arthritis associated with infection with one or more of Hepatitis C, *Chlamydia*, gonorrhoea, *Salmonella* or *Shigella*.

In one embodiment the arthritic disease is arthritis as part of a systemic inflammatory disease.

In one embodiment, the arthritis as part of a systemic inflammatory disease, such as an inflammatory disease selected from the group consisting of Systemic lupus erythematosus, mixed connective tissue disease, Still's disease, and Polymyalgia Rheumatica.

In one embodiment, the rheumatoid arthritis is juvenile rheumatoid arthritis (JRA). JRA is an autoimmune, non-infective, inflammatory joint disease of more than 6 weeks duration in children less than 16 years of age. The disease commonly occurs in children from the ages of 1 to 6, but it may develop as late as 15 years of age.

In one embodiment, the JRA is selected from the group consisting of pauciarticular JRA, systemic-onset JRA, polyarticular JRA, and seronegative spondylarthritis.

In one embodiment the present disclosure provides a composition comprising, separately or together, methotrexate (MTX), or a pro-drug thereof, and a compound of formula (I), (Ia) or (II) as defined herein, for use in the treatment of an arthritic disease selected from the group consisting of
- an auto-immune disease or an inflammatory disease that presents with joint inflammation
- inflammatory arthritis, such as inflammatory arthritis selected from the group consisting of Rheumatoid Arthritis (RA), Psoriatic Arthritis, and Ankylosing Spondylitis,
- degenerative arthritis, such as osteoarthritis,
- metabolic arthritis, such as gouty arthritis,
- reactive and/or infectious arthritis, such as arthritis associated with infection with one or more of Hepatitis C, *Chlamydia*, gonorrhoea, *Salmonella* or *Shigella*,
- arthritis as part of a systemic inflammatory disease, such as an inflammatory disease selected from the group consisting of Systemic lupus erythematosus, mixed connective tissue disease, Still's disease, and Polymyalgia Rheumatica,
- juvenile rheumatoid arthritis (JRA), such as JRA selected from the group consisting of pauciarticular JRA, systemic-onset JRA, polyarticular JRA, and seronegative spondylarthritis.

In one embodiment, the arthritic disease presents in association with synovitis.

Synovitis refers to inflammation of the synovial membrane, which is specialized connective tissue that lines the inner surface of capsules of synovial joints and tendon sheath.

In one embodiment the present disclosure provides a composition comprising, separately or together, methotrexate (MTX), or a pro-drug thereof, and a compound of formula (I), (Ia) or (II) as defined herein, for use in the treatment of joint inflammation.

In one embodiment the present disclosure provides a composition comprising, separately or together, methotrexate (MTX), or a pro-drug thereof, and a compound of formula (I), (Ia) or (II) as defined herein, for use in the treatment of synovitis.

In one embodiment, the arthritic disease is affecting one or more of joints in a hand, a knee, a hip, the spine, a wrist, an ankle, hips, a toe, and/or an elbow.

In one embodiment, the composition for use according to the present disclosure provides treatment of an arthritic disease, wherein the arthritic disease presents with one or more further symptoms selected from the group consisting of: joint stiffness, joint tenderness, inability to use a hand, inability to walk, malaise, fatigue, weight loss, poor sleep, muscle aches, pain, muscle weakness, loss of flexibility and decreased aerobic fitness.

In a particular embodiment the arthritic disease is undifferentiated polyarthritis (UP).

In a particular embodiment the arthritic disease is rheumatoid arthritis (RA). In one embodiment the present disclosure provides a composition comprising, separately or together, methotrexate (MTX), or a pro-drug thereof, and a compound of formula (I), (Ia) or (II) as defined herein, for use in the treatment of rheumatoid arthritis, RA.

In one embodiment, the rheumatoid arthritis is severe active RA (CDAI>22). In one embodiment, the rheumatoid arthritis is RA with a CDAI>22.

In one embodiment, the composition for use according to the present disclosure provides treatment of newly diagnosed subjects with severe active RA (CDAI>22).

In one embodiment, the rheumatoid arthritis is RA with a DAS28 score of above 5.1.

In one embodiment, the composition for use according to the present disclosure is provided, wherein the subject tests positive for rheumatoid factor and/or anti-cyclic citrullinated peptide (CCP) IgG antibodies prior to the treatment.

Subjects and Assessment of Disease Severity

The subject to be treated is preferably a mammal, in particular a human being. Treatment of animals, such as mice, rats, dogs, cats, horses, cows, sheep and pigs, is, however, also within the scope of the present disclosure. The subject to be treated can be of various ages.

The severity of arthritic disease, as well as the efficacy of medical treatment, of the subject can be assessed by a number of different clinical score systems, e.g. the DAS28 score, the CDAI score and the ACR-score.

For example, the change in one or more clinical scores after treatment can be evaluated by assessing the resulting chance in said clinical scores, and comparing same to baseline or placebo.

There are a wide range of measures of disease activity in RA including:
- examination of the subject's joints for swelling and tenderness (Swollen Joint Count, SJC, and Tender Joint Count, TJC),
- global scores of pain and overall status of the subject,
- blood markers of inflammation (e.g. Erythrocyte sedimentation rate (ESR or sed rate) that indirectly measures the degree of inflammation present in the body of the subject, and the c-reactive protein test that measures the level of c-reactive protein (CRP) in the blood of the subject)

questionnaires (e.g. the Health Assessment Questionnaire Disability Index (HAQ-DI, which assesses subject function) & Functional Assessment of Chronic Illness Therapy-Fatigue (FACIT-Fatigue), Imaging techniques such as X-ray imaging, ultrasound imaging, and magnetic resonance imaging (MRI).

In one embodiment, the treatment according to the present disclosure results in improved physical function in the subject as determined by the Health Assessment Questionnaire Disability Index (HAQ-DI).

In one embodiment, the treatment according to the present disclosure results in improved function in the subject as determined by the Functional Assessment of Chronic Illness Therapy-Fatigue (FACIT-Fatigue).

In one embodiment, the composition for use according to the present disclosure results in partial or complete remission of one or more arthritis symptoms.

In one embodiment, the composition for use according to the present disclosure reduces joint inflammation.

In one embodiment, the composition for use according to the present disclosure reduces the level of c-reactive protein (CRP) in the blood.

In one embodiment, the composition for use according to the present disclosure reduces the number of tender joints and/or reduces the number of swollen joints.

DAS28 Score

The DAS28 score is a measure of disease activity in rheumatoid arthritis (RA). DAS stands for 'disease activity score' and the number 28 refers to the 28 joints that are examined in this assessment.

The DAS28 is a composite score derived from 4 of the above measures. This '28' version is a simplification of the original DAS score, which requires 44 joints to be counted. Other versions of the DAS28 allow the CRP to be used instead of the ESR, or the omission of either. The DAS28-CRP, part of the many DAS scores for RA, is very useful to make an objective, reproducible and comparable assessment of the rheumatoid arthritis activity. DAS28-CRP in particular takes into account the following items:

TJC28: The number of tender joints (0-28).
SJC28: The number of swollen joints (0-28).
CRP: The C-Reactive Protein level (in mg/l).
GH: The patient global health assessment (from 0=best to 100=worst).

The 28 tender or swollen joint scores target the same joints (shoulders, elbows, wrists, metacarpophalangeal joints, proximal interphalangeal joints and the knees). The computation of the score can be done through the following equation:

$$DAS28_{CRP}=0.56*\sqrt{TJC28}+0.28*\sqrt{SJC28}+0.36*\ln(CRP+1)+0.014*GH+0.96$$

Generally, remission is considered achieved if the score is between 0 and <2.6. Low disease activity corresponds to 2.6 to <3.2. Moderate disease activity is between 3.2 and 55.1, while high disease activity is strictly above 5.1.

In one embodiment, the composition as disclosed herein for use in the treatment of an arthritic disease, such as RA, is provided, wherein the Disease Activity Score 28 (DAS28) is determined for the subject prior to and after treatment, wherein the treatment results in a reduced DAS28 score, such as wherein the treatment results in a DAS28 score below 5.1, such as 5.0 or less, such as 4.8 or less, such as 4.6 or less, such as 4.4 or less, such as 4.2 or less, such as 4.0 or less, such as 3.8 or less, such as 3.6 or less, such as 3.4 or less, such as 3.2 or less, such as 3.0 or less, such as 2.8 or less, such as 2.6 or less, such as 2.4 or less, such as 2.2 or less, such as 2.0 or less, such as 1.8 or less, such as 1.6 or less, such as wherein the treatment results in a DAS28 score below 5.1, preferably 3.2 or less, more preferably 2.6 or less.

In one embodiment the composition according to the present disclosure is administered to a subject with a DAS28 score of 5.1 or above. In one embodiment said subject's DAS28 score during and/or after treatment is reduced to between 3.2 and 55.1 (moderate activity), such as reduced to between 2.6 to <3.2 (low activity), such as reduced to between 0 and <2.6 (remission).

In one embodiment the composition according to the present disclosure is administered to a subject with a DAS28 score of between 3.2 and 55.

In one embodiment the composition according to the present disclosure is administered to a subject with a DAS28 score of between 2.6 to <3.2.

In a preferred embodiment, the DAS28 score is reduced to below 3.2 by the treatment of the present disclosure (low disease activity). In a preferred embodiment, the DAS28 score is reduced to below 2.6 by the treatment of the present disclosure (remission).

CDAI Score

The CDAI (Clinical Disease Activity Index) is a useful clinical composite score for following patients with rheumatoid arthritis. The CDAI is the sum of 4 outcome parameters: tender and swollen joint counts (28 joints assessed) and patient's and physician's global assessments of disease activity (on a 0-10-cm visual analog scale). The CDAI is the same as the Simplified Disease Activity Index (SDAI), except that the SDAI includes the C-reactive protein level.

Descriptive changes in CDAI where CDAI=SJC (28)+TJC (28)+PGA+IGA;

SJC (28): Swollen 28-Joint Count (shoulders, elbows, wrists, MCPs, PIPs including thumb IP, knees);

TJC (28): Tender 28-Joint Count (shoulders, elbows, wrists, MCPs, PIPs including thumb IP, knees);

PGA: Patient Global Disease Activity (patient's self-assessment of overall RA disease activity on a scale 0-100 where 100 is maximal activity);

IGA: Physician's Global Disease Activity (evaluator's assessment of the subject's overall RA disease activity on a scale 0-100 where 100 is maximal activity)

Remission is considered achieved if the score is between 0 and <2.8; Low disease activity corresponds to 2.8 to <10. Moderate disease activity is between 10 and 522, while high disease activity is strictly above 22 (CDAI>22).

In one embodiment the composition according to the present disclosure is administered to a subject with a CDAI score of 22 or above. In one embodiment said subject's CDAI score during and/or after treatment is reduced to between 10 and 522 (moderate activity), such as reduced to between 2.8 to <10 (low activity), such as reduced to between 0 and <2.8 (remission).

In one embodiment the composition according to the present disclosure is administered to a subject with a CDAI score of between 10 and 522.

In one embodiment the composition according to the present disclosure is administered to a subject with a DAS28 score of between 2.8 to <10.

In one embodiment said subject's CDAI score during and/or after treatment result in a 5-point decrease, such as a 10-point decrease, such as a 15-point decrease.

In a preferred embodiment, the CDAI score is reduced to below 10 by the treatment of the present disclosure (low disease activity). In a preferred embodiment, the DAS28 score is reduced to below 2.8 by the treatment of the present disclosure (remission).

In a preferred embodiment, the CDAI score is reduced by 5 points or more, such as 10 points or more, such as 15 point or more.

ACR-Score

The ACR (American College of Rheumatology) Criteria is a standard criterion to measure the effectiveness of various arthritis medications or treatments in clinical trials for RA.

The ACR response rates ACR20, ACR50, and ACR70 are defined as ≥20%, ≥50% and ≥70% improvement, respectively, in swollen and tender joint counts (SJC/TJC) and 3 of the following 5 assessments: Patient's Global Assessment of Disease Activity, Physician's Global Assessment of Disease Activity, Patient's Assessment of Pain, Health Assessment Questionnaire (HAQ-DI), and C-Reactive Protein (CRP).

In a preferred embodiment, the ACR-score is improved by the treatment of the present disclosure In a preferred embodiment, the present therapy result in a ≥20%, a ≥50% or ≥70% improvement in ACR response rates.

In one embodiment the present disclosure provides a composition comprising, separately or together, methotrexate (MTX), or a pro-drug thereof, and a compound of formula (I), (Ia) or (II) as defined herein, for use in a method of
- improving physical function in a subject with arthritic disease, as determined by the Health Assessment Questionnaire Disability Index (HAQ-DI),
- improving function in a subject with arthritic disease, as determined by the Functional Assessment of Chronic Illness Therapy-Fatigue (FACIT-Fatigue),
- inducing partial or complete remission of one or more arthritis symptoms,
- reducing joint inflammation,
- reducing the level of c-reactive protein (CRP) in the blood,
- reducing the number of tender joints and/or reduces the number of swollen joints
- reducing the DAS28-score, such as reducing the DAS28-score to between 3.2 and 55.1 (moderate disease activity), such as reducing to between 2.6 to <3.2 (low disease activity), such as reducing to between 0 and <2.6 (remission),
- reducing the CDAI-score, such as reducing the CDAI-score to between 10 and ≥22 (moderate disease activity), such as reducing to between 2.8 to <10 (low disease activity), such as reducing to between 0 and <2.8 (remission),
- reducing the CDAI-score 5 points or more, such as 10 points or more, such as 15 point or more,
- improving the ACR-score, such as improving ACR response rates ≥20%, ≥50% or ≥70%, and/or
- decreasing MTX concentration and/or improving MTX response in a subject with arthritic disease, such as RA.

MTX Response

Methotrexate (MTX) remains the disease-modifying antirheumatic drug of first choice in rheumatoid arthritis (RA), but response varies. In observational studies approximately 30% of patients discontinue MTX in the medium term—around half due to inefficacy and half due to adverse events.

Predicting non-response to MTX could enable earlier access to alternative or additional medications and control of disease progression. In a recent study 43% of patients with RA were classified as MTX non-responders (Sergeant et al. Arthritis Research & Therapy (2018) 20:147).

Non-response to MTX treatment at 6 months can be defined as "no response" using the EULAR (European League Against Rheumatism) response criteria i.e. Disease Activity Score in 28 joints (DAS28) improvement ≤0.6, or DAS28 improvement >0.6 but ≤1.2 and 6-month DAS28>5.1.

The definition of non-response at 6 months embraced those who remained on the drug but had not exhibited enough improvement to be classified as moderate or good responders and also those who had discontinued the drug due to inefficacy, or started a bDMARD (biological DMARD—disease-modifying antirheumatic drug).

"Moderate" or "good" responders by the clinical score criteria are considered responders, as are patients who discontinued MTX by 6 months due to remission.

In one embodiment an MTX non-responder is predicted using a model predicting non-response in patients to identify an individual at high risk of non-response, such as the model disclosed by Sergeant et al 2018. Baseline predictors of non-response in their multivariable logistic regression model are RF (rheumatoid factor) negativity, higher HAQ (Health Assessment Questionnaire) score, higher tender joint count, higher HADS (Hospital Anxiety and Depression Scale) anxiety score and lower disease activity (lower baseline DAS28-CRP).

In one embodiment the present disclosure provides a composition comprising, separately or together, methotrexate (MTX), or a pro-drug thereof, and a compound of formula (I), (Ia) or (II) as defined herein, such as AP1189, for use in the treatment of an arthritic disease, such as RA, in an MTX non-responder.

In one embodiment an MTX non-responder is selected from the group consisting of
- a subject with non-response to treatment at 6 months
- a subject with non-response to treatment at 6 months defined as "no response" using the EULAR response criteria,
- a subject with non-response to treatment at 6 months evaluated as a Disease Activity Score in 28 joints (DAS28) improvement ≤0.6, or DAS28 improvement >0.6 but ≤1.2 and 6-month DAS28>5.1,
- a subject who discontinued MTX by 6 months, i.e. had stopped MTX and did not plan to restart, due to inefficacy,
- a subject with one or more baseline predictors of non-response selected from RF (rheumatoid factor) negativity, higher HAQ (Health Assessment Questionnaire) score, higher tender joint count (TJC28), higher HADS (Hospital Anxiety and Depression Scale) anxiety score and lower disease activity (lower baseline DAS28-CRP),
- an individual at high risk (or probability) of non-response, as determined by the model disclosed by Sergeant et al 2018,
- a female,
- a current smoker, and
- a person with high BMI.

In one embodiment the present disclosure provides a composition comprising, separately or together, methotrexate (MTX), or a pro-drug thereof, and a compound of formula (I), (Ia) or (II) as defined herein, such as AP1189, for use in the treatment of an arthritic disease, such as RA, in a subject with a low or insignificant response to MTX.

In one embodiment, the composition for use according to the present disclosure is provided, wherein treatment with MTX and a compound of formula (I), (Ia) or (II) as defined herein is initiated essentially at the same time.

In one embodiment, the composition for use according to the present disclosure is provided, wherein treatment with MTX is continued and treatment with a compound of formula (I), (Ia) or (II) as defined herein, is initiated at the time of defining the subject as an MTX non-responder.

In one embodiment, the composition for use according to the present disclosure is provided, wherein the subject has received MTX for treatment of an arthritic disease, such as RA, prior to co-treatment with the compound of formula (I), (Ia) or (II), as defined herein. In one embodiment, the MTX treatment has been suboptimal before initiation of treatment with the compound of formula (I), (Ia) or (II).

Dosage

In one embodiment the present disclosure provides a composition comprising, separately or together, methotrexate (MTX), or a pro-drug thereof, and a compound of formula (I), (Ia) or (II) as defined herein, for use in the treatment of an arthritic disease, wherein said MTX and said compound are each provided in a therapeutically effective amount.

A combination treatment for use as provided herein may allow for reduced toxicity in the subject, preferably by administration of a lower dose of methotrexate than the dose used by solo administration of methotrexate in the treatment of an arthritic disease.

Alternatively, a combination treatment for use as provided herein may allow for increased effect in the subject, preferably by enhancing the effect of methotrexate compared to solo administration of methotrexate in the treatment of an arthritic disease.

In one embodiment, the composition for use according to the present disclosure is provided, wherein the methotrexate (MTX) or prodrug thereof is administered in an amount of about 1 to about 30 mg per week, for example about 15 mg per week.

In one embodiment, the composition for use according to the present disclosure is provided, wherein the methotrexate (MTX) or prodrug thereof is administered in an amount of 1 to 1.5 mg/week, such as 1.5 to 2, such as 2 to 2.5, such as 2.5 to 3, such as 3 to 3.5, such as 3.5 to 4, such as 4 to 4.5, such as 4.5 to 5, such as 5 to 5.5, such as 5.5 to 6, such as 6 to 6.5, such as 6.5 to 7, such as 7 to 7.5, such as 7.5 to 8.5, such as 8.5 to 9, such as 9 to 9.5, such as 9.5 to 10, such as 10 to 10.5, such as 10.5 to 11, such as 11 to 11.5, such as 11.5 to 12, such as 12 to 12.5, such as 12.5 to 13, such as 13 to 13.5, such as 13.5 to 14, such as 14 to 14.5, such as 14.5 to 15, such as 15 to 15.5, such as 15.5 to 16, such as 16 to 16.5, such as 16.5 to 17, such as 17 to 17.5 such as 17.5 to 18, such as 18 to 18.5 such as 18.5 to 19, such as 19 to 19.5, such as 19.5 to 20, such as 20 to 20.5, such as 20.5 to 21, such as 21 to 21.5, such as 21.5 to 22, such as 22 to 22.5, such as 22.5 to 23, such as 23 to 23.5, such as 23.5 to 24, such as 24 to 24.5, such as 24.5 to 25, such as 25 to 25.5, such as 25.5 to 26, such as 26 to 26.5, such as 26.5 to 27, such as 27 to 27.5, such as 27.5 to 28, such as 28 to 28.5, such as 28.5 to 29, such as 29 to 29.5, such as 29.5 to 30 mg/week.

In one embodiment, the composition for use according to the present disclosure is provided, wherein the methotrexate (MTX) or prodrug thereof is administered in a weekly amount of about 5 to 10 mg, 5 to 15 mg, 10 to 15 mg, 5 to 20 mg, 10 to 20 mg, 10 to 25 mg, or 15 to 20 mg.

In one embodiment, the composition for use according to the present disclosure is provided, wherein the methotrexate (MTX) or prodrug thereof is administered in an oral dosage form in an amount of about 10 to about 25 mg once per week/weekly. Once per week means once every 7 days, preferably on the same week day.

In one embodiment, the composition for use according to the present disclosure is provided, wherein the methotrexate (MTX) or prodrug thereof is administered subcutaneously in an amount of about 5 to about 25 mg once per week/weekly. Once per week means once every 7 days, preferably on the same week day.

In one embodiment, the composition for use according to the present disclosure is provided, wherein the compound of formula (I), (Ia) or (II) is administered in an amount of about 1 mg to about 1000 mg per day, for example about 500 to about 1000 mg per day, such as about 50 to about 800 mg per day In one embodiment, the composition for use according to the present disclosure is provided, wherein the compound of formula (I), (Ia) or (II) is administered in an amount of 1 to 5 mg, 5 to 10 mg, 10 to 15 mg, 15 to 20 mg, 20 to 30 mg, 30 to 60 mg, 60 to 80 mg, 80 to 100 mg, 100 to 130 mg, 130 to 160 mg, 160 to 200 mg, 200 to 240 mg, 240 to 280 mg, 280 to 320 mg, 320 to 360 mg, 360 to 400 mg, 400 to 440 mg, 440 to 500 mg, 500 to 560 mg, 560 to 620 mg, 620 to 680 mg, 680 to 740 mg, 740 to 800 mg, 800 to 860 mg, 860 to 920 mg, 920 to 980 mg, 980 to 1000 mg/day.

In one embodiment, the composition for use according to the present disclosure is provided, wherein the compound is {3-[1-(2-nitrophenyl)-1H-pyrrol-2-yl]-allylidene}-aminoguanidine, for example (E)-N-trans-{3-[1-(2-nitrophenyl)-1H-pyrrol-2-yl]-allylidene}-aminoguanidine, or a pharmaceutically acceptable salt thereof, such as (E)-N-trans-{3-[1-(2-nitrophenyl)-1H-pyrrol-2-yl]-allylidene}-aminoguanidinium acetate (AP1189), and said compound is administered in an amount of 50 g, such as 100 mg, for example 200 mg, such as 400 mg, for example 600 mg, such as 800 mg once daily.

In one embodiment there is provided a composition comprising, separately or together, methotrexate (MTX) and (E)-N-trans-{3-[1-(2-nitrophenyl)-1H-pyrrol-2-yl]-allylidene}-aminoguanidinium acetate (AP1189), for use in the treatment of an arthritic disease, such as rheumatoid arthritis (RA), wherein said compound is administered in an amount of about 50 g, such as 100 mg, for example 200 mg, such as 400 mg, for example 600 mg, such as 800 mg once daily, and said MTX is administered orally in an amount of about 10 to about 25 mg once weekly, or wherein said MTX is administered subcutaneously in an amount of about 5 to about 15 mg once weekly.

In a preferred embodiment MTX or a prodrug thereof is administered once weekly. Commercially available dosage forms of MTX are available, for oral administration or subcutaneous administration. Both are to be administered one a week, preferably on the same week day.

In a preferred embodiment the compound of formula (I), (Ia) or (II) is administered daily, such as once daily, twice daily or three times daily.

In one embodiment, the composition comprising, separately or together, methotrexate (MTX), or a pro-drug thereof, and a compound of formula (I), (Ia) or (II) as defined herein, is administered for 1 week such as more than 1 week, such as 2 weeks or more than 2 weeks, such as 3 weeks or more than 3 weeks, such as 4 weeks or more than 4 weeks, such as for 1 month or more than 1 month, such as 2 months or more than 2 months, such as 3 months or more than 3 months, such as 4 months or more than 4 months, such as 5 months or more than 5 months, such as 6 months or more than 6 months, such as for more than 1 year.

In one embodiment, the composition for use according to the present disclosure is provided, wherein the (co-)administration of the compound of formula (I), (Ia) or (II) allows for administration of MTX, or a prodrug thereof, at a sub-therapeutic dosage, or a reduced dosage (i.e. a dosage that is lower than normally prescribed).

In one embodiment, the treatment with the compound of formula (I), (Ia) or (II) and MTX, or a prodrug thereof, is synergistic. In one embodiment, the treatment with the compound of formula (I), (Ia) or (II) and MTX, or a prodrug thereof, is additive.

In one embodiment, the administration of a compound of formula (I), (Ia) or (II) as defined herein, such as AP1189, and MTX, or a prodrug thereof, result in a synergistic effect.

In one embodiment, the administration of a compound of formula (I), (Ia) or (II) as defined herein, such as AP1189, and MTX, or a prodrug thereof, result in an interaction to produce a combined effect greater than the sum of their separate effects.

In a particular embodiment, the composition for use according to the present disclosure is provided, wherein the compound of formula (I), (Ia) or (II) is administered daily and the MTX, or a prodrug thereof, is administered weekly.

In one embodiment, the composition for use according to the present disclosure is provided, wherein the compound of formula (I), (Ia) or (II) is administered prior to and/or simultaneously with and/or after MTX, or a prodrug thereof.

In one embodiment, the composition for use according to the present disclosure is provided, wherein treatment with MTX is discontinued for a period of time, while treatment with the compound of formula (I), (Ia) or (II) is continued.

Formulations

The composition for use in the treatment of an arthritic disease comprises, separately or together, a compound of formula (I), (Ia) or (II), and methotrexate (MTX) or a prodrug thereof, in any suitable formulation.

In one embodiment, the composition for use according to the present disclosure is provided, wherein the MTX, or a prodrug thereof, is formulated for oral administration, such as in the form of tablets or capsules.

In one embodiment, the MTX, or a prodrug thereof, is formulated as a liquid. A liquid may be suitable for intravenous administration or injection, such as for subcutaneous injection.

In one embodiment, the MTX, or a prodrug thereof, is formulated for extended release.

In one embodiment, the MTX, or a prodrug thereof, is formulated for immediate release.

In one embodiment, the composition for use according to the present disclosure is provided, wherein the compound of formula (I), (Ia) or (II) is formulated for oral administration, such as in the form of tablets or capsules.

In one embodiment, the compound of formula (I), (Ia) or (II) is formulated as a liquid, such as a liquid for intravenous administration or continuous infusion, or a liquid for injection.

In one embodiment, the composition for use according to the present disclosure is provided, wherein the compound of formula (I), (Ia) or (II) is formulated for extended release. In one embodiment, the compound of formula (I), (Ia) or (II) is formulated for immediate release.

In one embodiment, the composition for use according to the present disclosure is provided, wherein the compound of formula (I), (Ia) or (II) is formulated for oral administration; and the MTX, or a prodrug thereof, is formulated for oral, intravenous, intramuscular or subcutaneous administration.

In a particular embodiment the composition for use according to the present disclosure is provided, wherein the compound of formula (I), (Ia) or (II) is formulated for oral administration.

In a particular embodiment the composition for use according to the present disclosure is provided, wherein the compound is {3-[1-(2-nitrophenyl)-1H-pyrrol-2-yl]-allylidene}-aminoguanidine, for example (E)-N-trans-{3-[1-(2-nitrophenyl)-1H-pyrrol-2-yl]-allylidene}-aminoguanidine, or a pharmaceutically acceptable salt thereof, such as (E)-N-trans-{3-[1-(2-nitrophenyl)-1H-pyrrol-2-yl]-allylidene}-aminoguanidinium acetate (AP1189), and said compound is formulated for oral administration.

In one embodiment said compound is formulated as an solid oral dosage form, such as a tablet.

In one embodiment said compound is formulated as a powder, such as an oral powder, such as an oral powder suitable for suspension in a liquid.

In one embodiment said compound is formulated as a suspension comprising dissolved oral powder.

In one embodiment said compound is formulated as an oral suspension, such as a suspension for oral administration.

Composition

In an also aspect of the present disclosure to provide a composition, such as a pharmaceutical composition, comprising, separately or together, methotrexate (MTX), or a pro-drug thereof, and a compound of formula (I) or (Ia):

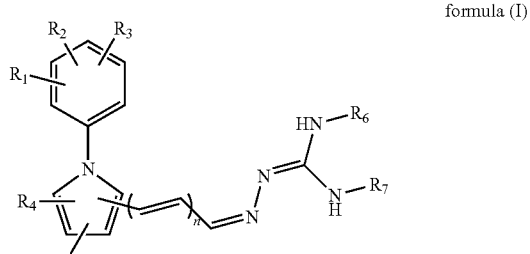

formula (I)

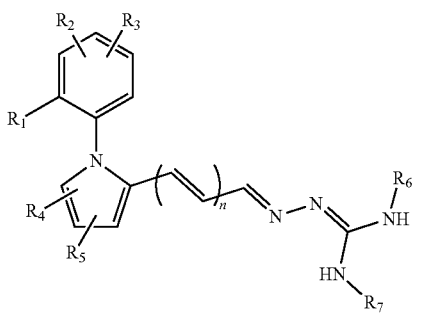

formula (Ia)

including tautomeric and isomeric forms, such as enantiomeric forms, diastereomeric forms and racemic forms, thereof;

wherein n is 1, 2 or 3;

each $R_1$, $R_2$, $R_3$, $R_4$ and $R_5$ is independently selected from the group consisting of hydrogen, optionally substituted $C_{1-6}$-alkyl, optionally substituted $C_{3-6}$-cycloalkyl, optionally substituted $C_{2-6}$-alkenyl, optionally substituted $C_{4-6}$-alkadienyl, optionally substituted $C_{2-6}$-alkynyl, hydroxy, optionally substituted $C_{1-6}$-alkoxy, optionally substituted $C_{2-6}$-alkenyloxy, carboxy, optionally substituted $C_{1-6}$-alkoxycarbonyl, optionally substituted $C_{1-6}$-alkylcarbonyl, formyl, $C_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroaryloxycarbonyl, optionally substituted heteroaryloxy, optionally substituted heteroarylcarbonyl, optionally substituted heteroarylamino, heteroarylsulphonylamino, optionally substituted heterocyclyl, optionally substituted heterocyclyloxycarbonyl, optionally substituted heterocyclyloxy, optionally substituted heterocyclylcarbonyl, optionally substituted heterocyclylamino, heterocyclylsulphonylamino, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkylamino-$C_{1-6}$-alkyl-aminocarbonyl, $C_{1-6}$-alkylcarbonylamino, amino-$C_{1-6}$-alkyl-carbonylamino, mono- and di($C_{1-6}$-alkyl)amino-$C_{1-6}$-alkyl-carbonylamino, cyano, guanidino, carbamido, $C_{1-6}$-alkanoyloxy, $C_{1-6}$-alkylsulphonyl, $C_{1-6}$-alkylsulphinyl, $C_{1-6}$-alkylsulphonyl-oxy, aminosulfonyl, mono- and di($C_{1-6}$-alkyl)aminosulfonyl, nitro, optionally substituted $C_{1-6}$-alkylthio and halogen, where any nitrogen-bound $C_{1-6}$-alkyl is optionally substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino or guanidine;

each $R_6$ and $R_7$ is independently selected from the group consisting of hydrogen, optionally substituted $C_{1-6}$-alkyl, optionally substituted $C_{2-6}$-alkenyl, optionally substituted $C_{4-6}$-alkadienyl, optionally substituted $C_{2-6}$-alkynyl, optionally substituted $C_{1-6}$-alkoxycarbonyl, optionally substituted $C_{1-6}$-alkylcarbonyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, aminocarbonyl, mono- and di($C_{1-6}$-alkyl)aminocarbonyl, amino-$C_{1-6}$-alkyl-aminocarbonyl and mono- and di($C_{1-6}$-alkyl)amino-$C_{1-6}$-alkyl-aminocarbonyl; or $R_6$ and $R_7$ may together form a five- or six-membered nitrogen-containing ring;

or a pharmaceutically acceptable derivative thereof.

In one embodiment there is provided a composition, such as a pharmaceutical composition, comprising, separately or together, methotrexate (MTX), or a pro-drug thereof, and a compound of formula (II):

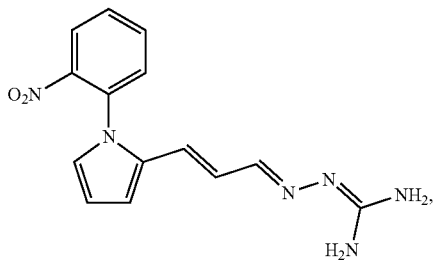

formula (II)

including tautomeric and isomeric forms, such as enantiomeric forms, diastereomeric forms and racemic forms, thereof; or a pharmaceutically acceptable derivative thereof.

In one embodiment there is provided a composition, such as a pharmaceutical composition, comprising, separately or together, methotrexate (MTX) and (E)-N-trans-{3-[1-(2-nitrophenyl)-1H-pyrrol-2-yl]-allylidene}-aminoguanidinium acetate (AP1189).

In one embodiment the present disclosure provides a composition comprising, separately or together, methotrexate (MTX), or a pro-drug thereof, a compound of formula (I), (Ia) or (II) as defined herein, and folic acid.

EXAMPLES

Example 1: Combination Treatment with Methotrexate and AP1189 ((E)-N-Trans-{3-[1-(2-nitrophenyl)-1H-pyrrol-2-yl]-allylidene}-aminoguanidinium acetate)

Materials & Methods

Six week-old C57/BL6 mice were purchased from Charles River and left for one week for acclimatization before starting the experiment.

Mice were randomly assigned to the following groups:
Group 1: Time control animals with no intervention
Group 2: Animals where arthritis was induced and where the animals were treated with vehicle to Methotrexate (vehicle 2) and AP1189 (vehicle 1)
Group 3: Animals where arthritis was induced and where the animals were treated with Methotrexate and vehicle to AP1189 (Vehicle 1)
Group 4: Animals where arthritis was induced and where the animals were treated with vehicle to Methotrexate (vehicle 2) and with AP1189
Group 5: Animals where arthritis was induced and where the animals were treated with Methotrexate and with AP1189

N=6 in all groups.

Arthritis was induced with two i.p. injections of 100 μl K/BxN serum on days 0 and 2 (for details see J Immunol 2015; 194:3381-3388).

AP1189 and Veh1 (20% PEG-200 in PBS) were administered orally from day 2 until day 7 orally in a total volume of 200 μl.

Methotrexate and Veh2 (12.5% carbonate) were administered on days 3, 5 and 7 by i.p. injection (injected volume: 200 μl).

Preparation of methotrexate formulation: A small volume of 0.1M carbonate-bicarbonate buffer pH=9.6 was used to dissolve methotrexate (Sigma Cat no: A6770). Then, PBS was used to reach the desired concentration. The final buffer resulted in 12.5% carbonate buffer. Diluted compound was divided in single-use aliquots and stored at −20° C. until use.

The development of arthritis was monitored daily from day 0 to day 8.

Mice were sacrificed on day 8 after recording the daily measurements.

K/BxN serum was produced by crossing KRN mice with NOD/Lt mice. The offspring develop spontaneous arthritis, evident at 6 weeks, with incidence of 100%. At week nine, serum was collected and stored at −80° C. until use, ie that the arthritis induced in the serum transfer model is due to administration of the collected serum to WT mice (for details see: Trends Mol Med, 2004; 10:40-5)

Visible signs of arthritis were assessed using the scoring method as described in Am J Pathol, 2014; 184(8):2333-41 consisting on assigning a score of 0-3 per paw, reaching a maximum of 12 per mouse:

Score 0: no signs of inflammation.
Score 1: subtle inflammation, localized.
Score 2: easily identified but localized.
Score 3: evident inflammation, not localized.

Clinical score was used to calculate the following parameters (for details see J Immunol, 2015; 194(7):3381-8)
- Arthritis incidence (mice showing overt signs of inflammation, i.e. score 1).
- Severe joints (number of paws per mouse that reached a maximum score of 3).
- Incidence of severe arthritis (number of mice with score>10).

Swelling in lower paws was measured using a plethysmometer (Ugo Basile).

Results

The incidence of severe arthritis was calculated as the % of mice in each group that reached a total score of 10.

None of animal in group 1 (the time controls where arthritis was not induced) developed arthritis.

In group 2, the vehicle treated animals with arthritis 5 out of 6 animals developed severe arthritis.

The incidence of severe arthritis in the animals treated with methotrexate (Group 3) or A P1189 (Group 4) alone was 50%.

Surprisingly, none of the animals treated with the combination of methotrexate and AP1189 developed severe arthritis.

Conclusion

Treatment of arthritis was surprisingly effective using a combination of methotrexate and AP1189 as none of the animals treated by the combination developed severe arthritis.

Example 2

Study

Figure 2:
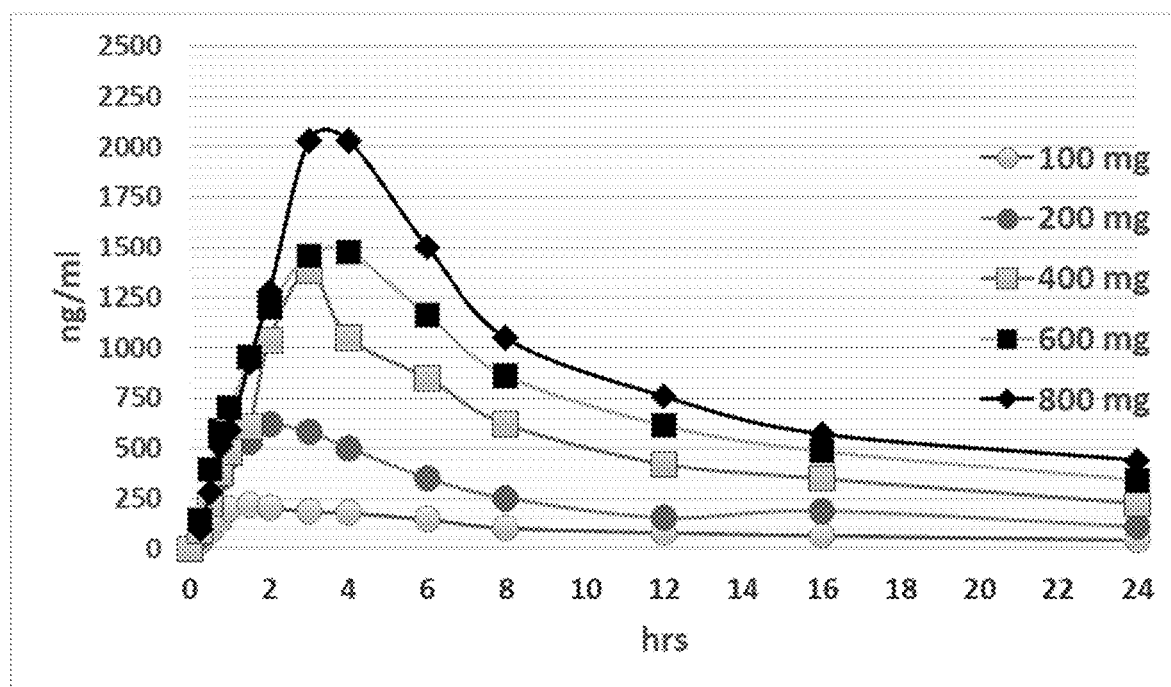
FIG. 2: Plasma concentration following single oral dosing of test compound in healthy volunteers. The test compound (AP1189) was given as a suspension in the morning to fasting male healthy volunteers. Dose levels of test compound: 100, 200, 400, 600 or 800 mg. Consecutive plasma samples were collected and concentration in plasma determined by LCMS-MS. N=6 per dose level. Mean per group.
Figure 3:
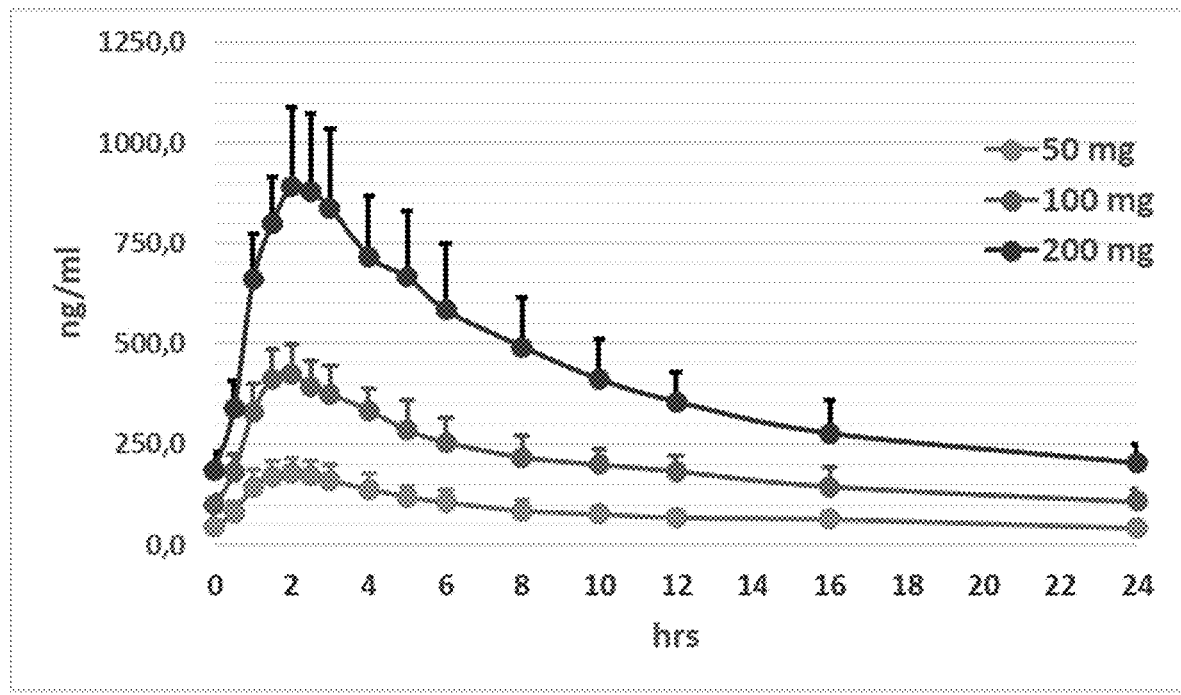
FIG. 3: Plasma concentration following repeated oral dosing of test compound in healthy volunteers. The test compound (AP1189) was given as a suspension in the morning to fasting male healthy volunteers once daily for two weeks. Dose levels of test compound 1: 50, 100, 200 mg. Consecutive plasma samples were collected following the last day of dosing (day 14) and concentration in plasma determined by LCMS-MS. N=9 per dose level. Mean+/−SD per group.

The first dose of AP1189 in healthy volunteers was administered in single ascending dosing using a suspension for oral administration (Part I—FIG. 2), in a bioequivalence study using oral suspension as well as tablets (Part II) and in 14 days repeated dosing (FIG. 3). Fourteen days repeated dosing was initiated using a tablet formulation (Part III) and was completed (Part IV) using the suspension for oral administration.

A total of 111 subjects were randomized; 104 young healthy male volunteers and eight (8) post-menopausal women. In Part I, 56 subjects received a single oral dose on one occasion (42 received AP1189 and 14 subjects received placebo). In Part II, eight (8) subjects received one single AP1189 oral dose in three occasions separated by one-week wash-out. In Part III, eleven (11) subjects received a single oral dose daily for 14 days (8 subjects received AP1189 and three (3) placebo) and in Part IV; thirty-six (36) subjects were treated with AP1189/placebo once daily for 14 days (27 subjects received AP1189, and nine (9) received placebo).

Summary of Study Results from Phase I; Part I, II and III

The study Parts I and II were completed. Study Part I was a randomized, double-blind, placebo-controlled, single ascending dose study with AP1189 or placebo administered as an oral suspension. Seven male groups with healthy volunteers (48 males), and 1 female group with 8 healthy female post-menopausal volunteers (defined by at least a two-year amenorrhea period and an FSH level >30 I.U/L.) received a single ascending dose with AP1189/placebo administered as an oral suspension of IMP dissolved in SyrSpend ALKA in fasting conditions. The two first male groups were composed of 3 subjects receiving active and one subject placebo; the other groups consisted of 6 subjects receiving active IMP and two subjects receiving placebo. Forty-eight (48) healthy male volunteers aged 19 to 39 years and eight (8) healthy postmenopausal female volunteers, aged 47 to 60 years were included.

The male subjects were treated with oral suspensions with doses in the range of 15-800 mg AP1189 (15 mg, 50 mg, 100 mg, 200 mg, 400 mg, 600 mg or 800 mg) or placebo. The females were treated with 400 mg AP1189 or placebo suspensions (See FIG. 2).

Pharmacokinetic (PK) results showed that in male subjects on the dose range 50-800 mg, AP1189 was rapidly absorbed with a median $t_{max}$ (time at which the $C_{max}$ is observed) between 1 and 4 hours. The inter-individual variability was low to moderate for $C_{max}$ (maximum plasma concentration) and AUCs (area under the curve) (<36%). Mean $t\frac{1}{2}$ was near to 20 h (CV %<20%).

Mean Vd/F was between 556 and 784 L with a CV % below 35% and mean CL/F was between 20.26 and 31.26 L/h with a CV % below 50%.

In female subjects, after administration of 400 mg of AP1189, $C_{max}$ and AUCs were slightly increased compared to male subjects. The apparent clearance was lower in the female population (17.26 L/h) and the apparent volume of distribution was similar. Statistically, no conclusion could be made on the gender effect.

Twenty (20) subjects reported a total of 38 Treatment-Emergent Adverse Events (TEAEs). All TEAEs were of mild (27) or moderate (11) severity. No severe AEs nor serious AEs were reported during the study. Twenty-two (22) of the 38 TEAEs were considered related to the study treatment: 21 of these events were after administration of 200 to 800 mg AP1189, and one event was after the administration of placebo.

The most frequent related TEAEs were gastrointestinal disorders (19 events reported by fourteen (14) subjects): nausea (7 events), abdominal pain (5 events), vomiting (3 events), diarrhea (2 events), abdominal distension (1 event) and dyspepsia (1 event). The frequency of these related TEAEs increased with the dose. Nevertheless, the amount of vehicle in the suspension increased with the dose leading to a consistency and taste increase of the study medicine. Amongst the TEAEs considered as not related, headache was reported by seven (7) subjects. Other TEAEs were sporadic.

Some mean changes and individual abnormalities were observed on laboratory parameters, vital signs, and ECG parameters. Most of these changes and abnormalities were limited and considered as not clinically significant.

A total of four (4) male subjects treated with AP1189 had isolated increases in aminotransferases (no concomitant changes in alkalic phosphatases or bilirubin were reported). The increases, which reached up to 1.6 above the normal upper value of ALT were observed in one (1) subject treated with 400 mg, two (2) subjects treated with 600 mg and one (1) subject treated with 800 mg. No increases in aminotransferases above the normal upper range were seen in placebo-treated subjects.

No treatment-related changes in vital signs were observed.

No AP1189 associated increases in QTcF (the corrected QT interval by Fredericia) nor changes in any other cardiac parameters were identified during continuous 24-hours 1000 HZ Holter ECG recording evaluation.

It was concluded that the maximum tolerated dose (MTD) was not reached. At the maximum administrated dose (MAD) the exposure obtained was more than 10× above what is expected to be the exposure level for obtaining therapeutic efficacy.

Study Part II

Study Part II was a comparative bioavailability study of an AP1189 tablet vs. the oral suspension with additional assessment of food effect following administration of the tablet, according to a three-way cross-over design. A 200 mg AP1189 dose, administered once as an oral suspension, and on two separate occasions as two 100 mg AP1189 tablets; once during fasting conditions and once after a high-fat breakfast were tested. The results following dosing with the suspension confirmed the findings from study part 1. Data from the administration of the tablet showed lower exposure with higher variability compared to data from the suspension.

Daily doses of AP1189 tablets of 100 mg (Group 1), 200 mg (Group 2) and 400 mg (Group 3) were investigated. Part III was designed as a randomized, double-blind, placebo-controlled, multiple ascending dose study with AP1189 administered as tablets.

The pharmacokinetic (PK) results obtained in Group 1 of the Study Part III, after a 14-day repeated dose, showed a high and unpredicted degree of bioavailability both within and between subjects. Exposure judged on Cmax was seen in the span from below the limit of quantification (BLQ) up to levels expected to be more than three times the exposure expected to induce therapeutic effects.

Study Part IV

A Part IV was added to the study that was identical to Study Part III but conducted with the oral suspension in fasting conditions.

Summary of Results from Part IV

Study Part IV was a randomized, double-blind, placebo-controlled, repeat dose study with AP1189 or placebo administered as an oral suspension given once daily for 14 days. Three cohorts of 12 subjects (9 on active; 3 on placebo) each were dosed with the same formulation as used in part 1 of the study. The dose levels tested were 50 mg, 100 mg or 200 mg with matching placebo (See FIG. 3).

PK, Part IV Cohort 1

The dose was 50 mg once daily. $C_{max}$ was observed between 1- and 2.5-hours post-dose regardless of the day of dosing. Steady state was achieved on Day 7 with $C_{max}$ around 180 ng/mL.

PK, Part IV Cohort 2

The dose was 100 mg once daily.

The PK analysis showed a steep increase in the plasma concentration and reached $C_{max}$ around 400 ng/ml at steady state, i.e., a peak increase by approximately 2-fold, when compared to findings in cohort 1.

PK, Part IV Cohort 3

The dose was 200 mg once daily. As for the two other cohorts, $C_{max}$ was reached within 1-2 hours post dosing. $C_{max}$ levels reached up to 900 ng/ml (group average) with the highest measured level of 1.300 ng/ml.

Safety from Part 4

Fourteen (14) subjects reported a total of 35 Treatment-Emergent Adverse Events (TEAEs). All TEAEs were of mild (27) or moderate (8) severity. No severe AEs nor serious AEs were reported during the study. Four (4) of the 35 TEAEs were considered possibly related to the study treatment. These 4 events were all related to gastrointestinal disorders were seen after administration of the investigational drug (two (2) in the same subject at the 50 mg dose level (one episode of diarrhea and one episode of abdominal cramp, two (2) in the same subject at the 200 mg dose level (one episode of nausea and one episode of vomiting). Amongst the TEAEs considered as not related, headache was reported by nine (9) subjects, seven (7) treated with the investigational drug and two (2) treated with placebo. Other TEAEs were sporadic.

Some mean changes and individual abnormalities were observed on laboratory parameters, vital signs, and ECG parameters. Most of these changes and abnormalities were limited and considered as not clinically significant. No individual QTcF clinically significant values were observed at any time of this study part in repeated standard 12 lead safety ECG.

A total of five (5) subjects all included in Cohort 3 (200 mg), three (3) treated with active and two (2) treated with placebo had isolated increases in aminotransferases (no concomitant changes in alkalic phosphatases or bilirubin were reported). The increases were most pronounced in the subjects treated with active where the increase reached up to 3.6× and 2.9× above the normal upper value (ALT). All values returned to normal following completion of the study.

It was concluded that MTD was not reached.

Example 3

In this study, the doses of 50 mg and 100 mg AP1189 are selected.

The peak respectively trough concentrations identified in the repeated dose part of the study with AP1189 were during steady conditions as follows:

|  | C Max (mean +/− SD, N = 9) | C Trough (Mean +/− SD, N = 9) |
|---|---|---|
| 50 mg once daily | 180 ± 38 ng/ml | 46 ± 14 ng/ml |
| 100 mg once daily | 427 ± 76 ng/ml | 100 ± 25 ng/ml |
| 200 mg once daily | 893 ± 198 ng/ml | 186 ± 45 ng/ml |

Primary Safety Endpoint

The safety of AP1189 against placebo by evaluating adverse events (AEs), serious adverse events (SAEs), and laboratory abnormalities.

Primary Efficacy Endpoint

The change in CDAI after 4 weeks of treatment compared to baseline will be evaluated by assessing the following, by treatment group:
  Mean change in CDAI from baseline to week 4
  Proportion of subjects with a change in CDAI score from severe (CDAI>22) to moderate (CDAI≤22) at week 4 compared to baseline.

Secondary Efficacy Endpoints

The effects of AP1189 against placebo will be evaluated by assessing the following by treatment group:
  Proportion of subjects achieving a reduction of more than 10 (ten) swollen and/or tender joints (SJC and TJC, summarized) at week 4 compared to baseline
  Proportion of subjects achieving a change in CDAI score at week 4 compared to baseline
    Proportion of subjects with a 5-point decrease
    Proportion of subjects with a 10-point decrease
    Proportion of subjects with a 15-point decrease
  Proportion of subjects achieving a change in DAS28 from DAS28>3.2 to DAS28≤3.2 at week 4 compared to baseline Change of HAQ-DI at week 4 compared to baseline
Change of FACIT-Fatigue at week 4 compared to baseline
Proportion of subjects achieving ACR response assessed by ACR 20, ACR 50, and AC70

Tertiary Efficacy Endpoints

The effect of A P1189 compared to placebo at week 4 compared to baseline will be further evaluated by assessing the following by treatment group:

CXCL13, IL-1β, IL-6, IL-10, and TNF-α
Synovial biopsy at baseline and after 4 weeks treatment (only Part 2 at selected sites).

Study Design

This study is a multicenter, two-part, randomized, double-blind, placebo-controlled, 4-week study with repeated doses of AP1189. The study population will consist of newly diagnosed subjects with severe active RA (CDAI>22) who are to start up-titration with MTX. A minimum of 90 subjects are expected to complete the study. Up to 120 subjects are planned to be enrolled to account for up to 25% discontinuation rate. Subjects who fulfill the enrollment criteria will be randomized in a 2:1 ratio in group A and B. One group will receive active treatment, and the other group will receive a placebo. Group C/D will have the same 2:1 ratio between active and placebo.

Group A (12 subjects): AP1189 dose 50 mg, once daily for 4 weeks (28 days) plus MTX (10-25 mg) weekly
Group B (6 subjects): placebo for 4 weeks (28 days) plus MTX (10-25 mg) weekly
Group C (12 subjects): AP1189 dose 100 mg, once daily for 4 weeks (28 days) plus MTX (10-25 mg) weekly
Group D (6 subjects): placebo for 4 weeks (28 days) plus MTX (10-25 mg) weekly Number of Subjects Part 1

A minimum of 36 subjects is expected to complete Part 1 of the study. About 48 subjects are planned to be enrolled in accounting for approximately 25% discontinuation rate.

Part 2

All subjects will be randomized into one design only, either design 1, 2, or 3

Design 1: AP1189 dose 50 mg (36 subjects) or placebo (18 subjects), once daily for 4 weeks (28 days) plus MTX (10-25 mg) weekly
Design 2: AP1189 dose 100 mg (36 subjects) or placebo (18 subjects), once daily for 4 weeks (28 days) plus MTX (10-25 mg) weekly
Design 3: Continue with the same doses as in Part 1, in a 1:1:1 ratio (AP1189 50 mg (18 subjects), AP1189 100 mg (18 subjects) or placebo (18 subjects)) plus MTX (10-25 mg) weekly Number of Subjects in Part 2

A minimum of 54 subjects is expected to complete Part 2 of the study. About 72 subjects are planned to be enrolled in accounting for approximately 25% discontinuation rate.

Study Duration

Total study duration is 18 months, and the study duration for each subject is approximately and up to 10 weeks.

Number of Investigational Sites

The study is to be conducted at sites in Europe.

Study Population

The study population will consist of subjects with severe active RA, defined as CDAI>22, who are about to begin up-titration with MTX.

Inclusion Criteria

1. Written informed consent has been obtained prior to initiating any study specific procedures
2. Male and female subjects, 18 to 85 years of age
3. Confirmed diagnosis of RA according to the 2010 ACR/EULAR RA classification criteria
4. Arthritis with joint swelling and tenderness of a minimum of three joints out of 68 joints tested
5. Candidate for MTX treatment
6. Is about to begin treatment with MTX
7. Tested positive for anti-CCP or RF
8. Severe active RA (CDAI>22) at screening and baseline
9. Negative QFG-IT (Mantoux test can be used if QFG-IT is not possible)
10. Subjects should be able to complete (read and write) the PRO questionnaires
11. Females of child-bearing potential may only participate if using reliable means of contraception (for detailed information see section 17.8) or are post-menopausal (menstrual periods stopped at least 12 months ahead of the enrolment in the trial). Surgically sterilized women at least 6 months prior to screening
12. Females of childbearing potential must have a negative pregnancy test at screening and baseline.

Exclusion Criteria

Subjects meeting any of the following criteria are not eligible for participation in the study:

1. Participation in any other study involving investigational drug(s) within 4 weeks prior to study entry
2. Major surgery (including joint operation) within 8 weeks prior to screening or planned surgery within 1 month following randomization
3. Rheumatic autoimmune disease other than RA, including SLE, MCTD, scleroderma, polymyositis, or significant systemic involvement secondary to RA (e.g., vasculitis, pulmonary fibrosis or Felty's syndrome). Sjögren syndrome with RA is allowable
4. Functional class IV as defined by the ACR Criteria for Classification of Functional Status in RA or wheelchair/bedbound
5. Prior history of or current inflammatory joint disease other than RA (e.g., gout, reactive arthritis, psoriatic arthritis, seronegative spondyloarthropathy, Lyme disease)
6. Subjects with fibromyalgia
7. Initiation or change in dose for NSAIDs (including low-dose aspirin and COX-2 inhibitors) within 2 weeks prior to dosing with the IMP
8. Corticosteroids are prohibited within 2 weeks prior to screening (and during the entire treatment period and until the final visit (Visit 7))
9. Evidence of serious uncontrolled concomitant cardiovascular, nervous system, pulmonary (including obstructive pulmonary disease), renal, hepatic, endocrine (including uncontrolled diabetes mellitus), or gastrointestinal disease
10. Have prior renal transplant, current renal dialysis or severe renal insufficiency (determined by a derived glomerular filtration rate (GFR) using Cockcroft Gault formula of ≤30 ml/min/1.73 m$^2$ calculated by the local lab)
11. Uncontrolled disease states, such as asthma, psoriasis, or inflammatory bowel disease where flares are commonly treated with oral or parenteral corticosteroids
12. Evidence of active malignant disease (except basal cell carcinoma of the skin that has been excised and cured)
13. Pregnant women or nursing (breastfeeding) mothers
14. History of alcohol, drug, or chemical abuse within the 6 months prior to screening 15. Neuropathies or other painful conditions that might interfere with pain evaluation
16. Body weight of >150 kg.
17. Evidence of moderate and/or severe organ dysfunction
18. Abnormal chest x-ray (as per the discretion of the investigator)
19. Evidence of positive hepatitis serology
20. Evidence of peptic ulcer disease The study drug information is presented in the below tables.

TABLE 1

Test Treatment

| Name | AP1189 |
|---|---|
| Dosage strength | 50 mg, 100 mg |
| Formulation | Powder |
| Route of | Oral |
| Supplier | SynAct Pharma |

TABLE 2

Reference Treatment

| Name | Placebo |
|---|---|
| Dosage strength | 0 mg |
| Formulation | Powder |
| Route of | oral |
| Supplier | SynAct Pharma |

Description of AP1189 Product:

IUPAC: E-N-[trans-3-{1-(2-nitrophenyl)-1H-pyrrole-2-yl}-allylideneamino] guanidinium acetate The substance is an acetic acid salt that appears as an odorless, yellow solid.

Structural formula

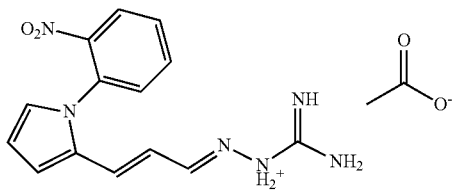

Molecular formula: $C_{16}H_{18}N_6O_4$

The molecular weight is 358.35 for the salt and 298.30 for the free base.

Methotrexate (MTX)

All subjects will follow the local guideline for starting treatment with MTX and continue MTX treatment throughout the study.

MTX Treatment Instruction in Case of Elevation in Liver Enzymes

It is recommended with more frequent blood test in case of elevation of liver enzymes.

Transaminase Increase:

| Laboratory Value | Action |
|---|---|
| ALT and/or AST increases up to >1 to ≤3 × Upper | IMP and MTX remains unchanged. It is recommended with more frequent blood test in case of elevation of liver enzymes. |

-continued

| Laboratory Value | Action |
|---|---|
| Limit of Normal (ULN) And bilirubin is within the normal range | |
| ALT and/or AST increases >3 to ≤5 × ULN And bilirubin is within the normal range | Pause IMP dosing until ALT and/or AST <3 × ULN and follow recommendations above for >1 to <3 × ULN Upon normalization of ALT and/or AST, IMP resumes For persistent increases >3 × ULN, discontinue IMP |
| ALT and/or AST >5 × ULN | MTX and IMP discontinue |
| Bilirubin > normal range | MTX and IMP treatment discontinue |

Folic Acid

It is possible that AEs commonly associated with MTX treatment will occur. To minimize MTX toxicity, all subjects treated with MTX should be on folic acid or equivalent at a dose of at least 5 mg/week according to local guidelines and at the discretion of the investigator. Folic acid can either be given as a single dose weekly or be divided into daily doses to achieve at least 5 mg folic acid per week.

Prohibited Medicines

The following CYP1A2 substrates are not permitted: Alosetron, Clozapine, Flutamide, Frovatriptan, Melatonin, Mexiletine, mirtazapine, Olanzapine, Ramelteon, Rasagiline, Ropinirole, Tacrine, Theophylline, Tizanidine, Triamterene and zolmitriptan Laboratory Assessments The latest updated reference ranges from the local laboratory will be used.

Hematology

Hemoglobin, white blood cell (WBC) count (total and differential: leukocytes, neutrophils, eosinophils, basophils, lymphocytes, monocytes), red blood cells (RBC), thrombocytes and hemoglobin A1c (HbA1C) The hematology blood samples will be taken at screening, baseline, after 2 weeks and 4 weeks treatment.

Biochemistry

Sodium, potassium, chloride, calcium, glucose, creatinine, urea, albumin, unconjugated and total bilirubin, aspartate transaminase (AST), alanine transaminase (ALT), alkaline phosphatase (ALP), gamma-glutamyl transferase (GGT) and INR. The biochemistry blood samples will be taken at all visits. A serum μ-HCG pregnancy test will be taken at screening.

Thyroid Function

Thyroxine (T4) free, triiodothyronine (T3) total or free, and the thyroid-stimulating hormone (TSH). Blood samples for measuring the thyroid function.

Urinalysis

A dipstick urine test for blood, protein, and glucose will be performed at the site at the Screening Visit. A urine sample may be sent for urine culture.

Serology

RF or anti-CCP, HBsAg, HBV antibody and HCV antibody.

RF is an antibody that is detectable in the blood of approximately 80% of adults with RA.

CRP is an acute phase reactant, a protein made by the liver and released into the blood within a few hours after tissue injury, the start of an infection, or other cause of inflammation. The CRP will most often be increased by inflammation.

One of the aims of treatment is to reduce the CRP to normal levels. CRP will be measured at screening, baseline, after 2 weeks and 4 weeks treatment.

Safety (AE and SAE)

Safety measures (AEs, SAEs, including laboratory abnormalities) will be registered during the whole study duration.

Safety Assessments (Sub-Study, Only Part 2)

The arthroscopy sub-study in Part 2, will assess the effect of 4 weeks treatment with AP1189/placebo compared to baseline by examining synovial fluid: (evaluating the change in the percentage of polymorphs, monocytes, and lymphocytes in synovial fluid).

In RA the immunohistological features of synovial inflammation change as the clinical manifestations change in response to conventional disease-modifying antirheumatic drugs, pulse methylprednisolone, or intra-articular glucocorticoids.

Efficacy Assessments

Swollen Joint Count (SJC) and Tender Joint Count (TJC)

An assessment of 66 joints for swelling and 68 joints for tenderness will be made at screening, baseline, after 2 weeks and 4 weeks treatment. Joints will be assessed and classified as swollen/not swollen and tender/not tender by pressure and joint manipulation on physical examination. The subject will be asked for pain sensations on these manipulations and watched for spontaneous pain reactions. Any positive response to pressure, movement, or both will then be categorized as tender-versus-nontender. Swelling is defined as palpable fluctuating synovitis of the joint. Swelling secondary to osteoarthrosis will be assessed as not swollen unless there is unmistakable fluctuation.

Joint assessments of one particular subject should be performed by the same assessor (if at all possible) throughout the trial to minimize inter-observer variation.

Clinical Disease Activity Index (CDAI)

The CDAI is a clinical composite score for following patients with RA.

Descriptive changes in CDAI where CDAI=SJC (28)+TJC (28)+PGA+IGA;

SJC (28): Swollen 28-Joint Count (shoulders, elbows, wrists, MCPs, PIPs including thumb IP, knees);

TJC (28): Tender 28-Joint Count (shoulders, elbows, wrists, MCPs, PIPs including thumb IP, knees);

PGA: Patient Global Disease Activity (patient's self-assessment of overall RA disease activity on a scale 0-100 where 100 is maximal activity);

IGA: Physician's Global Disease Activity (evaluator's assessment of the subject's overall RA disease activity on a scale 0-100 where 100 is maximal activity) The CDAI will be scored at screening, baseline, after 2 weeks and 4 weeks treatment.

Disease Activity Score 28 (DAS28)

The DAS28 is a combined index for measuring disease activity in RA. The index includes swollen and tender joint counts, CRP, and general health status. In this trial CRP will be used to calculate the DAS28 score. The index is calculated using the following formula:

$$DAS28-CRP(4)=0.56*sqrt(TJC28)+0.28*sqrt(SJC28)+0.36*ln(CRP+1)+0.014*GH+0.96$$

Where, TJC=tender joint count on 28 joints, SJC=swollen joint count on 28 joints, ln=natural log, CRP=C-reactive Protein, and GH=general health, i.e., patient's global assessment of disease activity (100-mm VAS).

The DAS28 provides an absolute indication of RA disease activity on a scale of 0.49 to 9.07

A DAS28 value >5.1 corresponds to a high disease activity

A DAS28 value between 3.2 and 5.1 corresponds to a moderate disease activity

A DAS28 value between 2.6 and 3.2 corresponds to a low disease activity

A DAS28 value <2.6 corresponds to remission

Compared to an initial value the disease activity of the subject can be classified as follows:

| | | DAS28 decrease from initial value | | |
|---|---|---|---|---|
| Current DAS28 | | >1.2 | >0.6 but ≤1.2 | ≤0.6 |
| ≤3.2 | Inactive | Good improvement | Moderate improvement | No improvement |
| >3.2 but ≤5.1 | Moderate | Moderate improvement | Moderate improvement | No improvement |
| >5.1 | Very active | Moderate improvement | No improvement | No improvement |

The DAS28 will be scored at baseline, after 2 weeks and 4 weeks treatment.

Physician's Global Assessment of Disease Activity VAS ("Investigator Global VAS")

The physician's assessment of the subject's current disease activity on a 100 mm horizontal VAS. The extreme left end of the line should be described as "no disease activity" (symptom-free and no arthritis symptoms) and the extreme right end as "maximum disease activity." The efficacy assessor should complete this. Investigator Global VAS will be measured at screening, baseline, after 2 weeks and 4 weeks treatment.

Patient's Global Assessment of Disease Activity VAS ("Patient Global VAS")

The subject's overall assessment of their current disease activity on a 100 mm horizontal VAS. The extreme left end of the line should be described as "no disease activity" symptom-free and no arthritis symptoms) and the extreme right end as "maximum disease activity" (maximum arthritis disease activity). Patient Global VAS will be measures at screening, baseline, after 2 weeks and 4 weeks treatment.

Patient's Assessment of Pain VAS ("Patient Pain VAS")

The subject's assessment of his/her current level of pain on a 100 mm horizontal VAS. The extreme left end of the line should be described as "no pain" and the extreme right end as "unbearable pain." Patient Pain VAS will be measured at screening, baseline, after 2 weeks and 4 weeks treatment.

Quality of Life and Physical Function

Functional Assessment of Chronic Illness Therapy-Fatigue (FACIT-Fatigue) The FACIT-Fatigue assessment is a 13-item questionnaire with subjects scoring each item on a 5-point scale. The assessment was originally developed for chronic illnesses and is now validated for patients with RA. FACIT-Fatigue will be scored at baseline, after 2 weeks and 4 weeks treatment.

Health Assessment Questionnaire—Disability Index (HAQ-DI)

HAQ-DI is a validated tool to evaluate physical function. It consists of 20 questions referring to 8 component sets: dressing/grooming, arising, eating, walking, hygiene, reach, grip, and activities. HAQ-DI will be scored at baseline, after 2 weeks and 4 weeks treatment.

American College of Rheumatology Response Rates

The ACR (American College of Rheumatology) Criteria is a standard criterion to measure the effectiveness of various arthritis medications or treatments in clinical trials for RA.

The ACR response rates ACR20, ACR50, and ACR70 are defined as ≥20%, ≥50% and ≥70% improvement, respectively, in swollen and tender joint counts (SJC/TJC) and 3 of the following 5 assessments: Patient's Global Assessment of Disease Activity (see above), Physician's Global Assessment of Disease Activity (see above), Patient's Assessment of Pain (see above), Health Assessment Questionnaire (HAQ-DI, see above), and C-Reactive Protein (CRP).

Pharmacokinetic Assessments

PK Sample Collection

Plasma PK samples for exposure-response analysis will be taken after 1, 2, 3- and 4-weeks treatment.

Cytokine Samples

Plasma samples for CXCL13, IL-1β, IL-6, IL-10, and TNF-α analysis will be taken at baseline, after 2 weeks and 4 weeks treatment.

Biobanking

The following samples are kept at frozen storage in a biobank or similar, as applicable per country, during the study:

Cytokines (CXCL13, IL-1β, IL-6, IL-10, and TNF-α), plasma

PK, plasma

Analysis of all cytokines and PK will be performed at a central laboratory. The samples will be sent and analyzed on a regular basis.

Safety

Severity Classification

The severity of an event is evaluated in order to subcategorize events. Severity is not seriousness. A very severe event can be non-serious, and a serious event can be of mild severity. Each event will be graded for severity using Common Terminology Criteria for Adverse Events (CTCAE), v4.03 grading scale: Jun. 14, 2010.

The following grading will apply:

Mild (Grade 1)—Mild; asymptomatic or mild symptoms; clinical or diagnostic observations only; intervention not indicated.

Moderate (Grade 2)—Moderate; minimal, local, or non-invasive intervention indicated; limiting age-appropriate instrumental Activity of Daily Living (ADL).

Severe (Grade 3)—Severe or medically significant but not immediately life-threatening; hospitalization or prolongation of hospitalization indicated; disabling; limiting self-care ADL.

Life-threatening (Grade 4)—Life-threatening consequences; urgent intervention indicated.

Death (Grade 5) related to AE.

A determination will be made of the relationship (if any) between an adverse event and the study drug. A causal relationship is present if a determination is made that there is a reasonable possibility that the adverse event may have been caused by the study drug.

REFERENCES

1. Perretti et al. Trends Pharmacol Sci. 36:737-55, 2015
2. Brzoska et al. Endocr Rev. 29:581-602, 2008
3. Montero-Melendez et al. Am J Pathol. 179:259-69, 2011
4. Catania et al., 2004
5. Garcia-Borron et al. Pigment Cell Res 18: 393-410, 2005
6. Slominski et al., 2000
7. Hunt et al., 1994
8. Abdel-Malek et al., 1995
9. Abdel-Malek, 2001
10. Manna and Aggarwal, 1998
11. Buckley and Ramachandran, 1981
12. Mountjoy et al., 1992
13. Xia and Wikberg, 1996
14. Boston, 1999
15. Chhajlani, 1996
16. Gantz et al., 1993
17. Roselli-Rehfuss et al., 1993
18. Getting, 2002
19. Li et al., 1996
20. Chen et al., 2000
21. Guarini et al., 2002
22. Getting and Perretti, 2000
23. Alvaro et al., 1996
24. Mountjoy et al., 1994
25. Marsh et al., 1999
26. Van der Ploeg et al., 2002
27. Taylor and Namba, 2001
28. Chen et al., 1997
29. Thody and Shuster, 1970
30. Lindskog et al., 2010.
31. Silman A J, Pearson J E, Epidemiology and genetics of rheumatoid arthritis. Arthritis Res. 2002; 4 Suppl 3:S265-72. Epub 2002 May 9
32. Gibofsky A. Overview of epidemiology, pathophysiology, and diagnosis of rheumatoid arthritis. Am J Manag Care 2012; 18:S295-302
33. Blumberg S, Fox D. Rheumatoid Arthritis: Guidelines for Emerging Therapies. Am J Manag Care. 2001; 7(6): 617-26.
34. Hirano T. The biology of interleukin-6. Chem immunol. 1992; 51:153-180
35. Keller T K, Wanagat J, Erschler W B. Molecular and cellular biology of interleukin-6 and its receptor. Frontiers Biosci. 1996; 1:340-357
36. Metzger S, Hassin T, Barash V, Pappo O, Chajek-Shaul T. Reduced body fat and increased hepatic lipid synthesis in mice bearing interleukin-6-secreting tumor. Am J Physiol Endocrinol Metab. 2001; 281:E597-E965
37. Tamura T, Udagawa N, Takahashi N, Miyaura C, Tanaka S, Yamada Y, et al. Soluble interleukin-6 receptor triggers osteoclast formation by interleukin-6. Proc Natl Acad Sci USA. 1993; 90:11924-11928
38. Taub R. Hepatoprotection via the IL-6/Stat3 pathway. J Clin Invest 2003; 112:978-980
39. Hirano T, Matsuda T, Turner M, Miyasaka N, Buchan G, Tang B, et al. Excessive production of IL-6/B cell stimulatory factor-2 in rheumatoid arthritis. Eur J Immunol. 1988; 18:1797-1801
40. Houssiau F A, Devogelaer J P, Van Damme J, de Deuxchaisnes C N, Van Snick J. IL-6 in synovial fluid and serum of patients with rheumatoid arthritis 50 and other inflammatory arthritides. Arthritis Rheum. 1988; 31:784-788
41. Madhok R, et al. The effect of second line drugs on serum interleukin 6 levels in rheumatoid arthritis. Arthritis Rheum. 1990; 33:S154. Abstract
42. Salaffi Fl, Cimmino M A, Leardini G, Gasparini S, Grassi W. Disease activity assessment of rheumatoid arthritis in daily practice: validity, internal consistency, reliability and congruency of the Disease Activity Score including 28 joints (DAS28) compared with the Clinical Disease Activity Index (CDAI). 2009 July-August; 27(4): 552-9

43. https://doi.org/10.1161/JAHA.116.003264. Journal of the American Heart Association. 2016; 5:e003264. Originally published Jun. 17, 2016
44. Rooney M, Whelan A, Feighery C, Bresnihan B Changes in lymphocyte infiltration of the synovial membrane and the clinical course of rheumatoid arthritis. Arthritis Rheum. 1989; 32:361-369
45. Walters M T, Smith J L, Moore K, Evans P R, Cawley M I D An investigation of the action of disease modifying anti-rheumatic drugs on the rheumatoid synovial membrane: reduction in T lymphocyte subpopulations and HLA-DP and DQ antigen expression after gold or penicillamine therapy. Ann Rheum Dis 1987; 30:1-10
46. Firestein G S, Paine M M, Littman B H Gene expression (collagenase, tissue inhibitor of metalloproteinases, complement and HLA-DR) in rheumatoid arthritis synovium. Quantitative analysis and effect of intra-articular corticosteroids. Arthritis Rheum 1991; 34:1094-1105
47. Firestein G S, Paine M M, Boyle D L Mechanism of methotrexate action in rheumatoid arthritis. Selective decrease in synovial collagenase gene expression. Arthritis Rheum 1994; 37:193-200
48. Yanni G, Farahat M N M R, Poston R N, Panayi G S Intramuscular gold decreases cytokine expression and macrophage numbers in the rheumatoid synovial membrane. Ann Rheum Dis 1994; 53:315-322
49. Youssef P P, Cormack J, Evill C A, Peter D T, Roberts-Thompson P J, Ahern M J, et al. Neutrophil trafficking into inflamed joints in patients with rheumatoid arthritis and the effect of methylprednisolone. Arthritis Rheum 1996; 39:236-242
50. Youssef P P, Haynes D R, Triantafillou S, Parker A, Gamble J R, Roberts-Thomson P J, et al. Effects of pulse methylprednisolone on inflammatory mediators in peripheral blood, synovial fluid, and synovial membrane in rheumatoid arthritis. Arthritis Rheum 1997; 40:1400-1408
51. Dolhain R J E M, Tak P P, Dijkmans B A C, de Kuiper P, Breedveld F C, Miltenburg A M M Methotrexate treatment reduced inflammatory cell numbers, expression of monokines and of adhesion molecules in synovial tissue of patients with rheumatoid arthritis. Br J Rheumatol 1998; 37:502-508
52. Bresnihan B, Tak P P Synovial tissue analysis in rheumatoid arthritis. Ballieres Clin Rheumatol 1999; 13:645-659
53. Non-Clinical Safety Studies for the Conduct of Human Clinical Trials for Pharmaceuticals (M3, rev 1). International Conference on Harmonization. Current Step 4 version, dated 9 Nov. 2000.
54. Sergeant et al. Arthritis Research & Therapy (2018) 20:147).

The invention claimed is:

1. A method of treating rheumatoid arthritis in a subject in need thereof, comprising administering to the subject:
   methotrexate (MTX) and
   an acetate salt of a compound of formula (II):

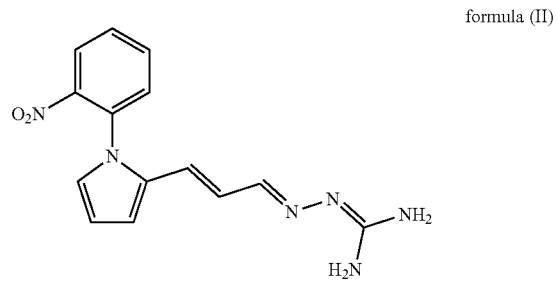 [SMILES: NC(N)=N/N=C/C=C/c1cccn1-c1ccccc1[N+](=O)[O-]]

formula (II)

or a tautomeric form thereof;
wherein the methotrexate (MTX) is administered once per week in an amount of about 1 to about 30 mg, and
wherein the acetate salt of the compound of formula (II) is administered once daily, twice daily, or three times daily in an amount of about 1 mg to about 1000 mg per day.

2. The method according to claim 1, wherein said acetate salt of the compound of formula (II) is (E)-N-trans-{3-[1-(2-nitrophenyl)-1H-pyrrol-2-yl]-allylidene}-aminoguanidinium acetate.

3. The method according to claim 1, wherein the rheumatoid arthritis (RA) is newly diagnosed severe active RA or juvenile rheumatoid arthritis (JRA).

4. The method according to claim 1, wherein the rheumatoid arthritis is characterized by a DAS28 score of above 5.1 and/or a CDAI>22.

5. The method according to claim 1, wherein the rheumatoid arthritis is characterized by a DAS28 score of 5.1 or above (high disease activity), a DAS28-score of between 3.2 and ≤5.1 (moderate disease activity), or a DAS28-score of between 2.6 to <3.2 (low disease activity).

6. The method according to claim 1, wherein the rheumatoid arthritis is characterized by a CDAI score of 22 or above (high disease activity), a CDAI-score of between 10 and ≤22 (moderate disease activity), or a CDAI-score of between 2.8 to <10 (low disease activity).

7. The method according to claim 1, wherein the rheumatoid arthritis is pauciarticular JRA, systemic-onset JRA, or polyarticular JRA.

8. The method according to claim 1, wherein:
   the rheumatoid arthritis presents itself in association with synovitis; or
   the rheumatoid arthritis affects one or more of joints in the hand, knee, hip, spine, wrist, ankle, hips, toe, and/or elbow; or
   the rheumatoid arthritis presents with one or more further symptoms selected from the group consisting of: joint stiffness, joint tenderness, inability to use a hand, inability to walk, malaise, fatigue, weight loss, poor sleep, muscle aches, pain, muscle weakness, loss of flexibility and decreased aerobic fitness.

9. The method according to claim 1, wherein the administration of the MTX and the acetate salt of the compound of formula II:
   i) reduces joint inflammation,
   ii) reduces the number of tender joints and/or reduces the number of swollen joints,
   iii) reduces the level of c-reactive protein (CRP) in the blood,
   iv) results in partial or complete remission of one or more arthritis symptoms, v) results in improved physical function in the subject as determined by the Health Assessment Questionnaire Disability Index (HAQ-DI),
vi) results in improved function in the subject as determined by the Functional Assessment of Chronic Illness Therapy-Fatigue (FACIT-Fatigue),
vii) reduces the DAS28 score,
viii) reduces the CDAI score,
ix) reduces the CDAI score by 5 points or more, or
x) results in a ≥20%, ≥50% or ≥70% improvement in ACR response rates;
xi) or a combination thereof.

10. The method according to claim 1, wherein the subject tests positive for rheumatoid factor and/or anti-cyclic citrullinated peptide (CCP) IgG antibodies prior to the administration of the MTX and the acetate salt of the compound of formula (II).

11. The method according to claim 1, wherein prior to the administration of the MTX and the acetate salt of the compound of formula (II), the responder subject is an MTX non-responder selected from the group consisting of
    a. a subject with non-response to a prior treatment with MTX at 6 months,
    b. a subject with non-response to a prior treatment with MTX at 6 months defined as "no response" using the EULAR response criteria,
    c. a subject with non-response to a prior treatment with MTX at 6 months evaluated as a Disease Activity Score in 28 joints (DAS28) improvement ≤0.6, or DAS28 improvement >0.6 but ≤1.2 and 6-month DAS28>5.1,
    d. a subject who discontinued a prior treatment with MTX by 6 months, i.e. had stopped MTX and did not plan to restart, due to inefficacy,
    e. a subject with one or more baseline predictors of non-response selected from RF (rheumatoid factor) negativity, higher HAQ (Health Assessment Questionnaire) score, higher tender joint count (TJC28), higher HADS (Hospital Anxiety and Depression Scale) anxiety score and lower disease activity (lower baseline DAS28-CRP),
    f. an individual at high risk (or probability) of non-response, as determined by the model disclosed by Sergeant et al 2018,
    g. a female,
    h. a current smoker, and
    i. a person with high BMI
    J. or a combination thereof.

12. The method according to claim 1, wherein when the acetate salt of the compound of formula (II) and the MTX are administered to the subject on the same day.

13. The method according to claim 1, further comprising administering folic acid to the subject.

14. The method according to claim 1, wherein the methotrexate (MTX) is administered once per week in an amount of about 10 to 25 mg or 5 to 15 mg and wherein the acetate salt of the compound of formula (II) is administered once daily, twice daily, or three times daily in an amount of about 50 mg, 100 mg, 200 mg, 400 mg, 600 mg, or 800 mg per day.

15. A method of treating rheumatoid arthritis in a subject in need thereof, comprising administering to the subject:
    methotrexate (MTX) and
    an acetate salt of a compound of formula (II):

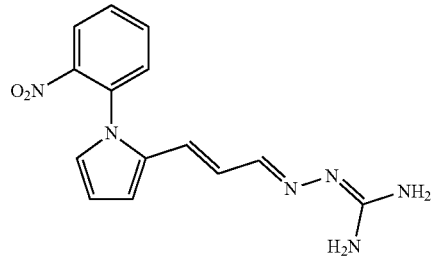

formula (II)

or a tautomeric form thereof;
wherein the administration of the MTX and the acetate salt of the compound of formula II:
i) reduces joint inflammation;
ii) reduces the number of tender joints and/or reduces the number of swollen joints;
iii) reduces the level of c-reactive protein (CRP) in the blood;
iv) results in partial or complete remission of one or more arthritis symptoms;
v) results in improved physical function in the subject as determined by the Health Assessment Questionnaire Disability Index (HAQ-DI);
vi) results in improved function in the subject as determined by the Functional Assessment of Chronic Illness Therapy-Fatigue (FACIT-Fatigue);
vii) reduces the DAS28 score to between 3.2 and ≤5.1 (moderate disease activity), reduces the DAS28 score to between 2.6 to <3.2 (low disease activity), or reduces the DAS28 score to between 0 and <2.6 (remission),
viii) reduces the CDAI score to between 10 and ≤22 (moderate disease activity), reduces the CDAI score to between 2.8 to <10 (low disease activity), reduces the CDAI score to between 0 and <2.8 (remission), reduces the CDAI score by 10 points or more, reduces the CDAI score of 15 points or more, or reduces the CDAI score by 5 points or more;
x) results in a ≥20%, ≥50% or ≥70% improvement in ACR response rates;
xi) or a combination thereof.

16. The method of claim 15, wherein the methotrexate (MTX) is administered once per week in an amount of about 1 to about 30 mg and wherein the acetate salt of the compound of formula (II) is administered once daily, twice daily, or three times daily in an amount of about 1 mg to about 1000 mg per day.

17. A method of treating rheumatoid arthritis in a subject in need thereof, comprising administering to the subject:
    methotrexate (MTX) and
    an acetate salt of a compound of formula (II):

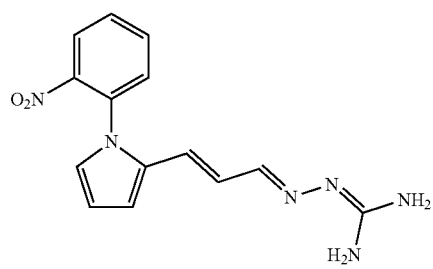

formula (II)

or a tautomeric form thereof;
wherein the acetate salt of the compound of formula (II) is administered simultaneously with the administration of the MTX.

18. The method of claim 17, wherein the methotrexate (MTX) is administered once per week in an amount of about 1 to about 30 mg and wherein the acetate salt of the compound of formula (II) is administered once daily, twice daily, or three times daily in an amount of about 1 mg to about 1000 mg per day.

* * * * *